United States Patent
Goel et al.

(10) Patent No.: US 10,947,537 B2
(45) Date of Patent: Mar. 16, 2021

(54) METHOD OF TREATING VEGF/VEGFR RESISTANT PROSTATE CANCER BY COMBINING THE THERAPY WITH RAC1 INHIBITORS

(71) Applicant: University of Massachusetts, Boston, MA (US)

(72) Inventors: Hira Lal Goel, Shrewsbury, MA (US); Arthur M. Mercurio, Boston, MA (US)

(73) Assignee: University of Massachusetts, Boston, MA (US)

( * ) Notice: Subject to any disclaimer, the term of this patent is extended or adjusted under 35 U.S.C. 154(b) by 139 days.

(21) Appl. No.: 16/076,981

(22) PCT Filed: Feb. 16, 2017

(86) PCT No.: PCT/US2017/018179
§ 371 (c)(1),
(2) Date: Aug. 9, 2018

(87) PCT Pub. No.: WO2017/143070
PCT Pub. Date: Aug. 24, 2017

(65) Prior Publication Data
US 2019/0040396 A1 Feb. 7, 2019

Related U.S. Application Data

(60) Provisional application No. 62/297,119, filed on Feb. 18, 2016.

(51) Int. Cl.
| | | |
|---|---|---|
| *C12N 15/113* | (2010.01) | |
| *C07K 14/00* | (2006.01) | |
| *C07K 16/22* | (2006.01) | |
| *C07K 14/47* | (2006.01) | |
| *A61K 31/506* | (2006.01) | |
| *A61K 31/404* | (2006.01) | |
| *A61P 35/00* | (2006.01) | |
| *A61K 31/7088* | (2006.01) | |
| *A61K 39/395* | (2006.01) | |

(52) U.S. Cl.
CPC ........ *C12N 15/1137* (2013.01); *A61K 31/404* (2013.01); *A61K 31/506* (2013.01); *A61K 31/7088* (2013.01); *A61K 39/3955* (2013.01); *A61P 35/00* (2018.01); *C07K 14/00* (2013.01); *C07K 14/4702* (2013.01); *C07K 16/22* (2013.01); *C12N 2310/11* (2013.01)

(58) Field of Classification Search
None
See application file for complete search history.

(56) References Cited

U.S. PATENT DOCUMENTS

| | | | |
|---|---|---|---|
| 7,482,002 B2 * | 1/2009 | Cedarbaum | C07K 14/71 424/134.1 |
| 2003/0211075 A1 | 11/2003 | Thorpe et al. | |
| 2012/0156202 A1 * | 6/2012 | Shantha | C07K 16/241 424/134.1 |
| 2014/0161720 A1 | 6/2014 | Garkavtsev et al. | |

OTHER PUBLICATIONS

Arnold et al., "Rac1 as a Multifunctional Therapeutic Target to Prevent and Combat Cancer Metastasis," Oncoscience, Aug. 2014, 1: 513-521.
Goel et al., "P-Rex1 Promotes Resistance to VEGF/VEGFR-Targeted Therapy in Prostate Cancer," Cell Reports, Feb. 2016, 14: 2193-2208.
Gonzalez-Villasana et al, "Rac1/Pak1/p38/MMP-2 Axis Regulates Angiogenesis in Ovarian Cancer," Clinical Cancer Research, Jan. 2015, 21; 2127-2137.
Hernandez et al., "Novel Inhibitors of Rac1 in Metastatic Breast Cancer," Puerto Rico Health Sciences Journal, Dec. 2010, 29: 348-356.
International Search Report and Written Opinion in International Application No. PCT/US2017/018179, dated Jul. 3, 2017, 23 pages.
Zhang et al., "PI3K p110α Isoform-Dependent Rho GTPase Rac1 Activation Mediates H2S-Promoted Endothelial Cell Migration via Actin Cytoskeleton Reorganization," PLoS One, Sep. 2012, 7; 1-13.
Baker et al., "Molecular pathways: targeting RAC-p21-activated serine-threonine kinase signaling in RAS-driven cancers," Clin Cancer Res, 2014, 20:4740-4746.
Bid et al., "RAC1: an emerging therapeutic option for targeting cancer angiogenesis and metastasis," Mol Cancer Ther, 2013, 12:1925-1934.
Cao et al., "Neuropilin-2 promotes extravasation and metastasis by interacting with endothelial alpha5 integrin," Cancer Res, 2013, 73:4579-4590.
Chatterjee et al., "Tumor VEGF:VEGFR2 autocrine feed-forward loop triggers angiogenesis in lung cancer," J Clin Invest, 2013, 123:1732-1740.
Civenni et al., "RNAi-mediated silencing of Myc transcription inhibits stem-like cell maintenance and tumorigenicity in prostate cancer," Cancer Res, 2013, 73:6816-6827.
Ferrara, "VEGF as a therapeutic target in cancer," Oncology, 2005, 69 Suppl: 3:11-16.
Garcia et al., "Pten null prostate epithelium promotes localized myeloid-derived suppressor cell expansion and immune suppression during tumor initiation and progression," Mol Cell Biol, 2014, 34:2017-2028.
Goel et al., "GLI1 regulates a novel neuropilin-2/alpha6beta1 integrin based autocrine pathway that contributes to breast cancer initiation," EMBO Mol Med, 2013, 5:488-508.
Goel and Mercurio, "VEGF targets the tumour cell," Nature Reviews, Dec. 2013, 13: 871-882.

(Continued)

*Primary Examiner* — Elly-Gerald Stoica
(74) *Attorney, Agent, or Firm* — Fish & Richardson P.C.

(57) ABSTRACT

Methods and compositions for treating cancer, e.g., prostate cancer, using a combination of P-Rex1 or Rac1 inhibitors and VEGF/VEGFR-targeted therapy.

8 Claims, 30 Drawing Sheets

Specification includes a Sequence Listing.

(56) References Cited

OTHER PUBLICATIONS

Goel et al., "VEGF/Neuropilin-2 Regulation of Bmi-1 and Consequent Repression of IGF-1R Define a Novel Mechanism of Aggressive Prostate Cancer," Cancer Discovery, 2012, 2:906-921.

Gu et al., "Hematopoietic cell regulation by Rac1 and Rac2 guanosine triphosphatases," Science, 2003, 302:445-449.

Kobayashi et al., "Activation of Rac1 is closely related to androgen-independent cell proliferation of prostate cancer cells both in vitro and in vivo," Mol Endocrinol, 2010, 24:722-734.

Liu and Strittmatter, "Semaphorin-mediated axonal guidance via Rho-related G proteins," Curr Opin Cell Biol, 2001, 13:619-626.

Luo et al., "Mammary epithelial-specific ablation of the focal adhesion kinase suppresses mammary tumorigenesis by affecting mammary cancer stem/progenitor cells," Cancer Res, 2009, 69:466-474.

Man et al., "Sema3C Promotes the Survival and Tumorigenicity of Glioma Stem Cells through Rac1 Activation," Cell Rep, 2014, 9:1812-1826.

Merino et al., "Antiangiogenic agents and endothelin antagonists in advanced castration resistant prostate cancer," Eur J Cancer, 2011, 47:1846-1851.

Michaelson et al., "Randomized, placebo-controlled, phase III trial of sunitinib plus prednisone versus prednisone alone in progressive, metastatic, castration-resistant prostate cancer," J Clin Oncol, 2014, 32:76-82.

Montalvo-Ortiz et al., "Characterization of EHop-016, novel small molecule inhibitor of Rac GTPase," J Biol Chem, 2012, 287:13228-13238.

Mulholland et al., "Lin-Sca-1+CD49fhigh stem/progenitors are tumor-initiating cells in the Pten-null prostate cancer model," Cancer Res, 2009, 69:8555-8562.

Pentheroudakis et al., "A study of gene expression markers for predictive significance for bevacizumab benefit in patients with metastatic colon cancer: a translational research study of the Hellenic Cooperative Oncology (HeCOG)," BMC Cancer, 2014, 14:111.

Qin et al., "Upregulation of PIP3-dependent Rac exchanger 1 (P-Rex1) promotes prostate cancer metastasis," Oncogene, 2009, 28:1853-1863.

Reese et al., "A Phase II Trial of Humanized Anti-Vascular Endothelial Growth Factor Antibody for the Treatment of Androgen-Independent Prostate Cancer," Prostate, 2001, J 3:65-70.

Riccomagno et al., "The RacGAP beta2-Chimaerin selectively mediates axonal pruning in the hippocampus," Cell, 2012, 149:1594-1606.

Ridgway et al., "Focal adhesion kinase is required for beta-catenin-induced mobilization of epidermal stem cells," Carcinogenesis, 2012, 33:2369-2376.

Sullivan et al., "r84, a novel therapeutic antibody against mouse and human VEGF with potent anti-tumor activity and limited toxicity induction," PLoS One, 2010, 5:e12031.

Tan et al., "An essential role for Rac 1 in endothelial cell function and vascular development," FASEB J, 2008, 22:1829-1838.

Tomic et al., "Castration resistant prostate cancer is associated with increased blood vessel stabilization and elevated levels of VEGF and Ang-2," Prostate, 2012, 72:705-712.

Wong et al., "Epigenetic regulation of phosphatidylinositol 3,4,5-triphosphate-dependent Rac exchanger 1 gene expression in prostate cancer cells," J Biol Chem, 2011 286:25813-25822.

Zhao and Guan, "Signal transduction by focal adhesion kinase in cancer," Cancer Metastasis Rev, 2009, 28:35-49.

Zhao et al., "VEGF drives cancer-initiating stem cells through VEGFR-2/Stat3 signaling to upregulate Myc and Sox2," Oncogene, 2014.

* cited by examiner

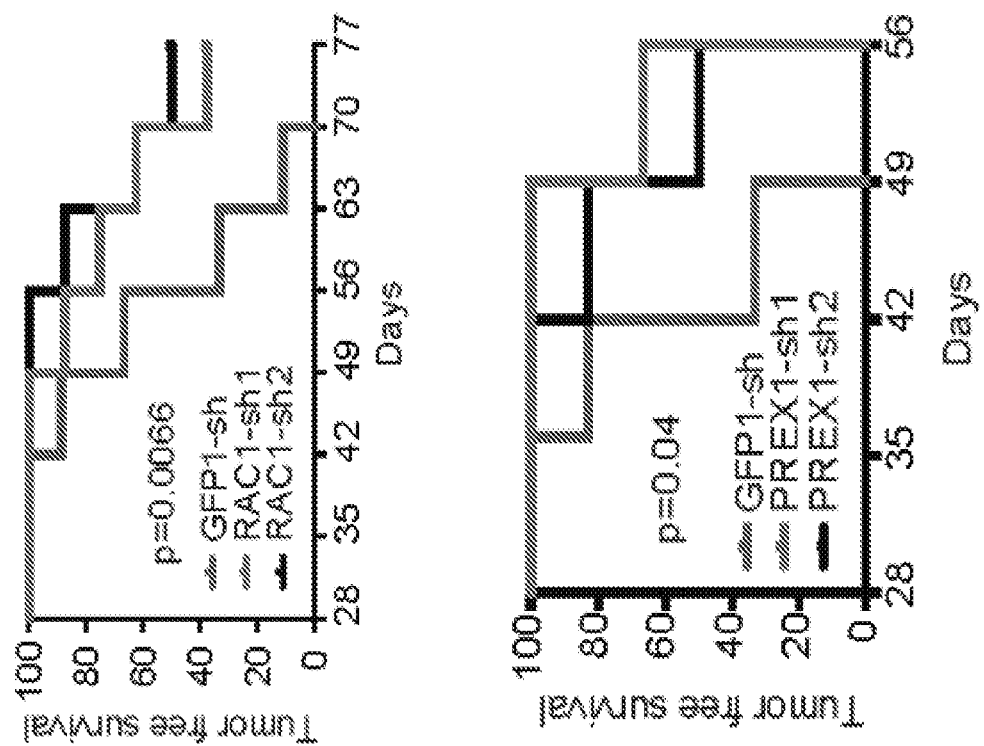
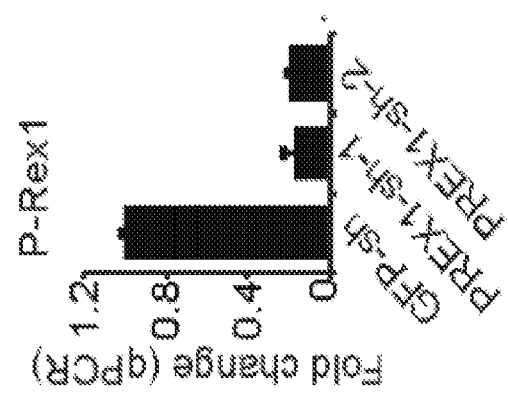
FIG. 7J
FIG. 7K

METHOD OF TREATING VEGF/VEGFR RESISTANT PROSTATE CANCER BY COMBINING THE THERAPY WITH RAC1 INHIBITORS

CLAIM OF PRIORITY

This application is a national phase application under 35 U.S.C. § 371 of PCT International Application No. PCT/US2017/018179, filed Feb. 16, 2017, which claims the benefit of U.S. Provisional Patent Application Ser. No. 62/297,119, filed on Feb. 18, 2016. The entire contents of the foregoing applications are hereby incorporated by reference.

FEDERALLY SPONSORED RESEARCH OR DEVELOPMENT

This invention was made with Government support under Grant Nos. CA168464, CA159856, GM094155 and CA034196 awarded by the National Institutes of Health and Grant No. W81XWH-12-1-0308 awarded by the Department of Defense. The Government has certain rights in the invention.

TECHNICAL FIELD

The disclosure relates to inhibiting Phosphatidylinositol 3, 4, 5-trisphosphate-dependent Rac exchanger 1 (P-Rex1) or Ras-related C3 botulinum toxin substrate 1 (Rac1) in combination with VEGF/VEGFR-targeted therapy for the treatment of cancer.

BACKGROUND

Vascular endothelial growth factor (VEGF) has emerged as an important factor in tumor initiation and progression. Its expression is elevated in many cancers, including aggressive prostate cancer. VEGF and VEGF receptors (VEGFR) are feasible therapeutic targets. However, many patients with prostate and other types of cancer do not respond well to VEGF/VEGFR-targeted therapy (Dror Michaelson, M., et al. "Randomized, Placebo-Controlled, Phase III Trial of Sunitinib Plus Prednisone Versus Prednisone Alone in Progressive, Metastatic, Castration-Resistant Prostate Cancer." Journal of clinical oncology 32.2 (2014): 76-82; Reese, David M., et al. "A Phase II Trial of Humanized Anti-Vascular Endothelial Growth Factor Antibody for the Treatment of Androgen-Independent Prostate Cancer." The Prostate Journal 3.2 (2001): 65-70). The reasons for the poor response to VEGF/VEGFR-targeted therapy are not well understood. There is a need to improve the response to VEGF/VEGFR-targeted therapy.

SUMMARY

The disclosure relates to inhibiting Phosphatidylinositol 3, 4, 5-trisphosphate-dependent Rac exchanger 1 (P-Rex1) or Ras-related C3 botulinum toxin substrate 1 (Rac1) in combination with VEGF/VEGFR-targeted therapy.

In one aspect, the disclosure relates to methods for treating cancer in a subject. The methods include administering to the subject a therapeutically effective amount of a VEGF/VEGFR-targeted therapy; and administering to the subject a therapeutically effective amount of a Ras-related C3 botulinum toxin substrate 1 (Rac1) inhibitor and/or a Phosphatidylinositol 3, 4, 5-trisphosphate-dependent Rac exchanger 1 (P-Rex1) inhibitor.

The disclosure also relates to methods of inducing apoptosis in a cancer cell. The methods include contacting the cancer cell with a VEGF/VEGFR-targeted therapy; and contacting the cancer cell with an effective amount of a Rac1 inhibitor and/or a Phosphatidylinositol 3, 4, 5-trisphosphate-dependent Rac exchanger 1 (P-Rex1) inhibitor.

In some embodiments, the VEGF/VEGFR-targeted therapy is an anti-VEGF antibody or anti-VEGF binding antibody fragment. In some embodiments, the VEGF/VEGFR-targeted therapy is bevacizumab, ranibizumab, mcr84, sunitinib, or pazopanib etc.

In some embodiments, the Rac1 inhibitor downregulates expression of Rac1. The Rac1 inhibitor can be an antisense molecule, a small interfering RNA, or a small hairpin RNA which is specific for a nucleic acid encoding Rac1. In some embodiments, the antisense molecule can be an oligonucleotide. In some embodiments, the Rac1 inhibitor can be EHT1864, NSC23766, W56, F56, a derivative of EHT1864 or NSC23766 etc. In some embodiments, the Rac1 inhibitor can include a CRISPR/Cas9 and Rac1-targeted guide RNA.

In some embodiments, the P-Rex1 inhibitor downregulates expression of P-Rex1. The P-Rex1 inhibitor can be an antisense molecule, a small interfering RNA, or a small hairpin RNA which is specific for a nucleic acid encoding P-Rex1. In some embodiments, the antisense molecule is an oligonucleotide. In some embodiments, the P-Rex1 inhibitor is an anti-P-Rex1 antibody or anti-P-Rex1 antibody fragment. In some embodiments, the P-Rex1 inhibitor can include a CRISPR/Cas9 and P-Rex1-targeted guide RNA.

In some embodiments, the cancer is prostate cancer, renal cell carcinoma, or colorectal cancer etc. In some embodiments, the cancer cell can be a prostate cancer cell, a renal carcinoma cell, or a colorectal cancer cell. In some embodiments, the cancer cell is a cancer stem cell.

As used herein, the term "Rac1 inhibitor" refers to any composition that inhibits Rac1. For example, a Rac1 inhibitor can block or reduce the activity of Rac1 protein, or inhibit the expression or translation of Rac1 gene. Exemplary Rac1 inhibitors include, but are not limited to, small molecules (e.g., EHT1864), antibody or antibody fragment that binds to Rac1, miRNA, shRNA, or siRNA that targets Rac1.

As used herein, the term "P-Rex1 inhibitor" refers to any composition that inhibits P-Rex1. For example, a P-Rex1 inhibitor can block the activity of P-Rex1 protein, or inhibit the expression or translation of P-Rex1 gene. Exemplary P-Rex1 inhibitors includes, but is not limited to, small molecules, antibody or antibody fragment that binds to P-Rex1, miRNA, shRNA, or siRNA that targets P-Rex1.

As used herein, the term "therapeutically effective amount" refers to a sufficient amount of an agent to treat a disease at a reasonable benefit/risk ratio applicable to a medical treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A. Cells from two human prostate tumors were sorted using CD44 and CD24 antibodies. Four subpopulations isolated based on expression of CD44 and CD24 were analyzed for their ability to form prostatospheres.

FIG. 1B. Four subpopulations isolated based on expression of CD44 and CD24 were analyzed for their sensitivity to bevacuzimab. The percentage of live cells in three different areas was determined and mean is plotted as cell survival.

FIG. 1C. Cells from two human freshly harvested prostate tumors were sorted using ITGA6 and ITGB4 antibodies. The four subpopulations isolated based on expression of ITGA6 and ITGB4 were analyzed for their ability to form prostatospheres and sensitivity to bevacuzimab. The percentage of live cells in three different areas was determined and mean is plotted as cell survival.

FIG. 1D. PC3 sensitive and resistant cells (1000 cells per 60 mm plate) were cultured in the presence of bevacizumab (1 mg/ml), sunitinib (20 μM) or their respective controls for 10 days and colonies were stained with crystal violet and colonies with more than 50 cells were counted.

FIG. 1E. C4-2 sensitive and resistant cells (1000 cells per 60 mm plate) were cultured in the presence of bevacizumab (1 mg/ml), sunitinib (20 μM) or their respective controls for 10 days and colonies were stained with crystal violet and colonies with more than 50 cells were counted.

FIG. 1F. PC3 and C4-2 resistant and sensitive cell lines were analyzed for colony formation in the presence or absence of 10 μM Pazopanib.

FIG. 1G. Resistant and sensitive PC3 and C4-2 populations were compared for their ability to form prostatospheres.

FIG. 1H. Resistant and sensitive PC3 populations were implanted into NSG mice and tumor onset was plotted.

FIG. 2A. Expression of Cell Stem Cell (CSC)-related genes and growth factor receptors was quantified by qPCR in resistant and sensitive populations of PC3 and C42 cells. Tables show fold change in mRNA expression upon normalization with sensitive populations, which were set as 1.

FIG. 2N. Sensitive PC3 cells were transfected with an HA-tagged, constitutively-active (CA) MEK construct and the effect on prostatosphere formation were analyzed.

FIG. 3A. Rac1 activation was compared in resistant and sensitive PC3 and C4-2 cells.

FIG. 3B. Resistant PC3 cells were transfected with a GST-tagged dominant-negative (DN) Rac1 construct, stimulated with VEGF and activation of ERK was analyzed by immunoblotting. GST expression indicates the level of DN-Rac expression.

FIG. 3C. Rac1 activation was measured in resistant PC3 cells in response to VEGF treatment in the presence of either a NRP inhibitory peptide (c-furSEMA) or control peptide (c-SEMA).

FIG. 3D. Resistant and sensitive PC3 cells were stimulated with VEGF and the effect on Rac1 activation and prostatosphere formation was measured.

FIG. 3E. VEGF expression was diminished in resistant PC3 and C4-2 cells using two different shRNAs and the effect on Rac1 activation was determined.

FIG. 3F. Either NRP1 or NRP2 was expressed in sensitive PC3 cells. These cells were stimulated with VEGF (50 ng/ml) for 30 minutes and the effect on Rac1 activation and prostatosphere formation was measured.

FIG. 3G. Resistant and sensitive PC3 cells were transfected with a GST-tagged, dominant-negative Rac construct (DN-Rac) or a constitutively active Rac construct (CA-Rac) and their effect on prostatosphere formation was measured.

FIG. 3H. PC3-R cells were stimulated with VEGF in the presence or absence of a Rac1 inhibitor (EHT1864; 20 μM) and the effect on prostatosphere formation was measured.

FIG. 3I. Freshly sorted Lin⁻Sca⁺CD49f$^{high}$ cells (LSC cells) from PTEN$^{pc-/-}$ mice were used to measure the effect of EHT1864, mcr84 or sunitinib on cell proliferation and prostatosphere formation.

FIG. 3J. Freshly sorted LSC cells from PTEN$^{pc-/-}$ mice were treated with EHT1864 (20 μM) and expression of genes associated with stem cells and VEGF signaling was quantified by qPCR.

FIG. 4A. Tumor volume of mice that were treated with either control IgG or bevacuzimab. PC3-R cells were transfected with Rac1 shRNAs and these cells were implanted in NSG mice. Once tumors reached approximately 100 mm³ in volume, mice were treated with either control IgG or bevacuzimab (10 mg/kg, intraperitoneally, twice weekly). Tumor volume was measured every third day.

FIG. 4B. Terminal deoxynucleotidyl transferase dUTP nick end labeling (TUNEL) for control and treated PC3-R xenograft tumors that were harvested. Apoptosis was analyzed using TUNEL staining. Scale bar is 10 μm.

FIG. 4C. Six-week old Pten$^{pc-/-}$ mice were injected (i.p.) with either mcr84 (10 mg/kg) or EHT1864 (10 mg/kg) twice weekly for three weeks. The GU tract was harvested and total weight was measured. The prostate glands were separated and combined weight of all the lobes was measured. The prostate glands were digested and LSC cells (Lin⁻Sca⁺CD49f$^{high}$) were isolated by FACS. The number of LSC cells is significantly reduced in mice treated with RACi or RACi+mcr84.

FIG. 4D. Six-week old Pten$^{pc-/-}$ mice were injected (i.p.) with either mcr84 (10 mg/kg) or EHT1864 (10 mg/kg) twice weekly for three weeks. The GU tract was harvested and total weight was measured. The prostate glands were separated and combined weight of all the lobes was measured.

FIG. 4E. Hematoxylin and eosin (H&E) staining of prostate tumors from Pten$^{pc-/-}$ mice described in FIG. 4C, and the percentage of prostate glands showing either PIN or well-differentiated adenocarcinoma (AdCa). Scale bar is 100 μm.

FIG. 4F. TUNEL staining of tumor sections of prostate tumors from Pten$^{pc-/-}$ mice described in FIG. 4C to detect apoptosis. Scale bar is 100 μm.

FIG. 5A. Expression of Rac1 GEFs that was compared in sensitive and resistant PC3 and C4-2 cell lines using qPCR. It shows fold change in mRNA expression upon normalization with sensitive populations, which was set as 1.

FIG. 5B. P-Rex1 was expressed in resistant PC3 cells in which VEGF expression had been diminished using shRNA and the effect on Rac activation was determined (left panel). P-Rex1 was expressed in resistant and sensitive PC3 cells and the effect on Rac activation was determined (middle panel). Right panels show the expression of HA-tagged P-Rex1 in PC3-R cells.

FIG. 5C. Resistant PC3 cells were transfected with either P-Rex1 shRNA or TIAM1 siRNA and the effect on Rac activation was determined.

FIG. 5D. Protein extracts from resistant PC3 cells in which VEGF expression that had been diminished using shRNA. Protein extracts were immunoblotted with P-Rex1, VEGF or actin antibodies.

FIG. 5E. Expression of NRP1 and NRP2. Either NRP1 or NRP2 was expressed in sensitive PC3 cells and the effect on P-Rex1 expression was assessed by immunoblotting.

FIG. 5F. Resistant PC3 cells were transfected with P-Rex1 shRNA and the effect on prostatosphere formation and Rac1 activation was analyzed.

FIG. 5G. Proliferation of resistant PC3 cells expressing P-Rex1 shRNA that were treated with bevacuzimab (1 mg/ml) or sunitinib (20 μM).

FIG. 5H. Expression of P-Rex1 that was analyzed in a published dataset (GSE56469).

FIG. 5I Expression of GEFs in freshly harvested LSC cells from 9-week old PTEN$^{pc-/-}$ mice by qPCR.

FIG. 5J. Expression of NRP2 and P-Rex1 mRNA. Expression was quantified by qPCR in microdissected sections from benign glands, as well as grade 3 and grade 5 prostate cancer specimens. A significant correlation (p value is 1×10⁻⁶) in the expression of P-Rex1 and NRP2 was observed (r=0.7).

FIG. 6A. PC3 cells were transfected with a GFP-expressing plasmid under control by the VEGF promoter and these cells were sorted based on their expression of GFP. The upper panels show FACS profile before GFP sorting and lower panels show FACS profile after sorting.

FIG. 6B. The ability of VEGF$^{high}$ and VEGF$^{low}$ cells to form colonies in soft agar was determined.

FIG. 6C. VEGF$^{high}$ and VEGF$^{low}$ cells were implanted in NSG mice and tumor formation was detected by palpation.

FIG. 6D. Expression of genes associated with stem cells and VEGF signaling was quantified by qPCR.

FIG. 6E. VEGF$^{high}$ and VEGF$^{low}$ cells were incubated with bevacuzimab (1 mg/ml) or sunitinib (20 μM) for 72 hours and their proliferation was assayed.

FIG. 6F. VEGF$^{high}$ and VEGF$^{low}$ cells were serum-deprived overnight and stimulated with VEGF (50 ng/ml) for 30 minutes in the presence or absence of bevacuzimab (5 mg/ml). The activation of ERK was analyzed by immunoblotting using a phospho-specific antibody.

FIG. 6G. Rac1 activation was compared in VEGF$^{high}$ and VEGF$^{low}$ cells.

FIG. 6H. NRP2 expression in VEGF$^{high}$ cells was down-regulated using shRNA and Rac1 activation was assayed.

FIG. 6I. Prostatosphere formation by VEGF$^{high}$ cells in the presence or absence of EHT1864 was quantified.

FIG. 6J. VEGF$^{high}$ cells were transfected with shRNAs targeting Rac1 and these cells were implanted in NSG mice. Tumor formation was detected by palpation.

FIG. 6K. VEGF$^{high}$ cells were transfected with shRNAs targeting P-Rex1 and these cells were implanted in NSG mice. Tumor formation was detected by palpation.

FIGS. 7A-7K. Myc regulates PREX1 transcription in resistant cells. FIG. 7A. A luciferase reporter construct containing the P-Rex1 promoter was expressed in sensitive and resistant PC3 and C4-2 cell and luciferase activity was measured and normalized to *Renilla*.

FIG. 7B. Myc expression was compared between sensitive and resistant PC3 and C4-2 cells by immunoblotting (left). VEGF expression was down-regulated in PC3-R cells using shRNAs and the effect on Myc expression activation was determined by immunoblotting (right).

FIG. 7C. Six-week old Pten$^{pc-/-}$ mice were injected (i.p.) with either mcr84 (10 mg/kg) twice weekly for three weeks. The prostate glands were harvested and immunostained using a myc antibody.

FIG. 7D. Myc expression was down-regulated in resistant PC3 and C4-2 cells using shRNA and the effect on Rac1 activation was determined.

FIG. 7E. Myc expression was down-regulated in PC3-R cells using shRNA and the effect on P-Rex1 expression was determined (left). Right: NRP2 expressing PC3-S cells were transfected with either GFP-sh or Myc-sh and stimulated with VEGF (50 ng/ml) for 24 hours and the effect on P-Rex1 and Myc expression was measured.

FIG. 7F. ChIP was performed using a Myc antibody and regions of the PREX1 promoter that bound Myc were identified and quantified by qPCR.

FIG. 7G. The expression of Myc and P-Rex1 was analyzed in human prostate cancer specimens by IHC. A significant correlation of their expression was detected. The Kappa estimate (0.45) is highly significant (P<0.0001) and it was tested against a null hypothesis of Kappa=0.0. Scale bar is 100 µm.

FIG. 7H. The ability of Myc-CaP cells to form colonies in soft agar in the presence or absence of EHT1864 was determined.

FIG. 7I. Myc-CaP cells were transfected with two different Rac1 shRNAs and the effect on Rac1 expression was detected by immunoblotting.

FIG. 7J. Myc-CaP cells were transfected with two different Rac1 shRNAs. These cells were implanted into NSG mice, and tumor onset was determined by palpation.

FIG. 7K. Myc-CaP cells were transfected with two different P-Rex1 shRNAs and the effect on P-Rex1 expression was quantified by qPCR (right). These cells were implanted into NSG mice, and tumor onset was determined by palpation (left).

FIG. 8A. PC3 (sensitive or resistant) cells were cultured in the presence of bevacizumab (1 mg/ml), sunitinib (20 µM) or their respective controls for 10 days and colonies were stained and photographed.

FIG. 8B. C4-2 (sensitive or resistant) cells were cultured in the presence of bevacizumab (1 mg/ml), sunitinib (20 µM) or their respective controls for 10 days and colonies were stained and photographed.

FIG. 8C. PC3 cells were cultured in the presence of bevacizumab (1 mg/ml), sunitinib (20 µM) or their respective controls for 72 hours and cell viability was analyzed using the MTT assay.

FIG. 8D. C4-2 cells were cultured in the presence of bevacizumab (1 mg/ml), sunitinib (20 µM) or their respective controls for 72 hours and cell viability was analyzed using the MTT assay.

FIG. 8E. PC3 and C4-2 cells were cultured in the presence of pazopanib (10 µM) or DMSO for 10 days and colonies were stained and photographed.

FIG. 8F. PC3 and C4-2 resistant and sensitive cell lines were cultured in the presence of pazopanib (10 µM) or DMSO for 72 hours and cell viability is analyzed using the MTT assay.

FIG. 9A. Surface expression of VEGFR2 in PC3-S and PC3-R cells was analyzed by flow cytometry.

FIG. 9B. VEGF expression was down-regulated using two independent shRNA in PC3-R cells and transfectants were cultured in the presence of bevacuzimab (1 mg/ml) for 10 days and colonies were stained with crystal violet. Colonies with more than 50 cells were counted and presented.

FIG. 9C. Expression of NRP2 and VEGF in sensitive and resistant populations of PC3 and C4-2 cells was assessed by immunoblotting.

FIG. 9D. PC3 and C4-2 resistant cells ($10^3$ cells per 60 mm plate) were cultured in the presence of either c-SEMA or c-furSEMA (1 µM), control IgG or NRP2 inhibitory antibody (1 µg/ml), or their respective controls for 10 days and colonies were stained with crystal violet. Colonies with more than 50 cells were counted.

FIG. 9E. Expression of either NRP1 or NRP2 was down-regulated in PC3-R cells using shRNAs. Subsequently, these cells were cultured for 10 days and number of colonies was counted (left panel). The expression of NRP1 and NRP2 mRNA was quantified by qPCR (right panel).

FIG. 9F. PC3 and C4-2 sensitive cells expressing NRP2 ($10^3$ cells per 60 mm plate) were cultured in the presence of IgG or bevacizumab (1 mg/ml), and VEGF for 10 days and colonies were stained with crystal violet and colonies with more than 50 cells were counted.

FIG. 9G. Freshly harvested LSC cells from 10-week old PTENpc−/− mice were analyzed for expression of VEGF, NRP1 and NRP2 using qPCR.

FIG. 9H. Ability of VEGF antibodies to block VEGF-A binding to NRP. Neither mcr84 nor bevacizumab blocked the binding of VEGF-A to NRP1. Only c-fur-Sema inhibited the interaction ($IC_{50}$=1.1 mM).

DETAILED DESCRIPTION

Figure 1A:
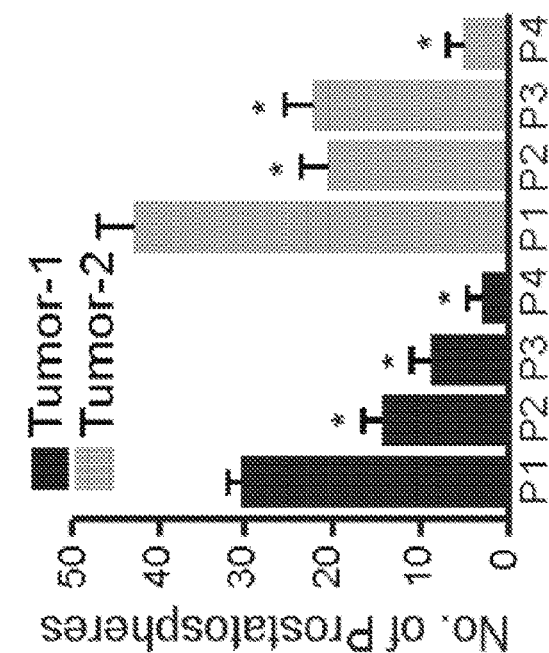
FIGS. 1A-1H. Characterization of prostate cancer cells resistant to VEGF/VEGFR-targeted therapy.
Figure 1A:
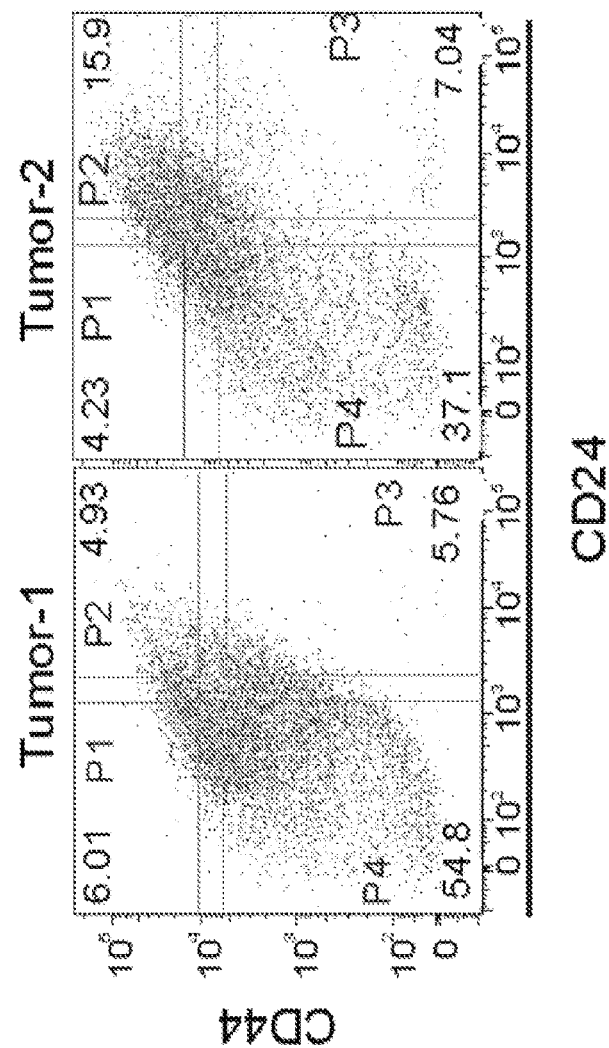

The present disclosure is based, at least in part, on the results from clinical trials concluding that bevacizumab and VEGF receptor tyrosine kinase inhibitors are not effective therapies for prostate cancer. VEGF signaling in tumor cells, especially cells with stem-like properties, is critical for tumor propagation and progression, and this signaling, mediated primarily by Neuropilins (NRPs), is a prime target for therapy. Indeed, as demonstrated herein, prostate cancer cells selected for their resistance to bevacizumab and sunitinib are enriched for stem cell properties and NRP signaling. Further, as demonstrated herein, NRP signaling in these cells induced expression of P-Rex1, a Rac1 GEF, and (without wishing to be bound by theory) Rac1-mediated ERK activation appears to be responsible for resistance to bevacizumab and sunitinib. These findings reveal a novel role for VEGF/NRP-mediated regulation of P-Rex1 in the biology of cancer stem cells (CSCs) and resistance to therapy.

Bevacizumab, a humanized VEGF antibody that blocks VEGF interactions with tyrosine kinase receptors (VEGFRs), and sunitinib, an inhibitor of VEGFRs and other receptors, have been used in clinical trials on prostate cancer patients. The prevailing assumption in these studies has been that these drugs target tumor angiogenesis. These trials did not yield a significant survival advantage, which has discouraged the use of these inhibitors for this disease. For example, the results from bevacizumab monotherapy were very disappointing with no response noted based on RECIST criteria, although 27% of patients exhibited a decline in PSA (Reese, D. M., Fratesi, B. S., Corry, M., Novotny, W., Holmgren, E., and Small, E. J. 2001. A Phase II Trial of Humanized Anti-Vascular Endothelial Growth Factor Antibody for the Treatment of Androgen-Independent Prostate Cancer. Prostate J 3:65-70). A recent study of 873 patients with aggressive prostate cancer found that the addition of sunitinib to prednisone did not improve overall survival compared with placebo (Michaelson, M. D., Oudard, S., Ou, Y C., Sengelov, L., Saad, F., Houede, N., Ostler, P., Stenzl, A., Daugaard, G., Jones, R., et al. 2014. Randomized, placebo-controlled, phase III trial of sunitinib plus prednisone versus prednisone alone in progressive, metastatic, castration-resistant prostate cancer. J Clin Oncol 32:76-82).

In addition to its contribution to endothelial biology and angiogenesis, VEGF signaling in tumor cells has emerged as an important factor in tumor initiation and progression. More specifically, compelling evidence now exists that autocrine VEGF signaling is necessary for the function of CSCs in prostate and other cancers (Goel, H. L., and Mercurio, A. M. 2013. VEGF targets the tumour cell. Nat Rev Cancer 13:871-882; Goel, H. L., Chang, C., Pursell, B., Leav, I., Lyle, S., Xi, H. S., Hsieh, C. C., Adisetiyo, H., Roy-Burman, P., Coleman, I. M., et al. 2012. VEGF/Neuropilin-2 Regulation of Bmi-1 and Consequent Repression of IGF-1R Define a Novel Mechanism of Aggressive Prostate Cancer Discovery 2:906-921). Given that CSCs have been implicated in resistance to therapy, tumor recurrence and metastasis, this role for VEGF signaling is significant and it appears to be independent of its function as a mediator of tumor angiogenesis. A hypothesis can be formulated from this information that the poor response of prostate tumors, especially aggressive tumors, to anti-VEGF (bevacizumab) and anti-VEGR therapy is that these therapies do not target CSCs effectively despite the fact that they are dependent on VEGF signaling.

An intriguing aspect of the present study is the 'VEGF paradox'. Specifically, as shown herein, resistance to VEGF/VEGFR-targeted therapy (bevacizumab and sunitinib) was mediated by an enhancement of VEGF/NRP signaling. In fact, prostate cancer cells treated with bevacizumab and sunitinib exhibited a marked increase in VEGF expression despite the fact that bevacizumab targets the interaction of VEGF with VEGF receptor tyrosine kinases. These data show that neither bevacizumab nor sunitinib was effective at targeting prostate cancer cells with stem cell properties and that the CSC population, which was characterized by autocrine VEGF/NRP signaling, was enriched by treatment with these drugs because they target primarily non-CSCs. In light of the present data that resistant cells showed a lack of VEGF2 surface expression, it is proposed that NRP2-mediated VEGF signaling is independent of its role as a co-receptor for VEGFRs. Moreover, without wishing to be bound by theory, NRP2 is believed to associate with the α6β1 integrin and to regulate CSC properties by activating FAK; this provides a potential mechanism for VEGF signaling that is independent of VEGFRs because FAK is known to mediate ERK activation and is important for CSCs.

The present data revealed an unexpected role for P-Rex1 and Rac1 activation in the genesis of prostate CSCs and resistance to bevacizumab and sunitinib. P-Rex1 is quite interesting in this regard because its expression is low in normal prostate and elevated in metastatic disease. There is also evidence that P-Rex1 can promote metastasis in a xenograft model of prostate cancer. The present results showed that P-Rex1-mediated Rac1 activation was critical for the formation and function of prostate CSCs. This conclusion is demonstrated most rigorously by the observation that treatment of mice harboring PTEN$^{pc-/-}$ tumors with a Rac1 inhibitor significantly reduced the number of Lin$^-$Sca$^+$CD49f$^{high}$ cells (LSC cells), which have been characterized as CSCs in this transgenic model. Also, treatment of these mice with the Rac1 inhibitor reduced the frequency of tumor formation, consistent with a role for Rac1 in the function of CSCs. Again without wishing to be bound by theory, also provided herein is evidence that Rac1-mediated activation of ERK is responsible for resistance to bevacizumab and sunitinib.

Figures 12A, 12B, 12C:
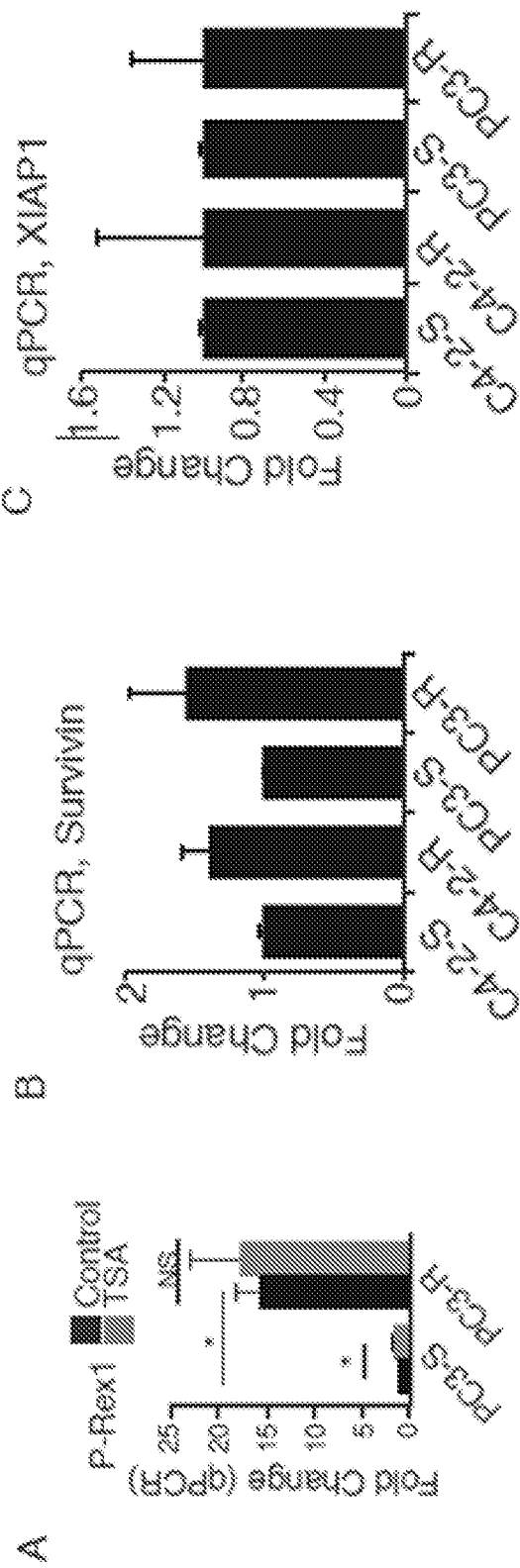
FIG. 12A. PC3-S and PC3-R cells were treated with TSA (a histone deacetylase inhibitor, 500 nM) for 24 hours. P-Rex1 mRNA expression was quantified by qPCR.
FIG. 12B. The expression of surviving was compared in sensitive and resistant PC3 and C4-2 cell lines using qPCR.
FIG. 12C. The expression of XIAP1 was compared in sensitive and resistant PC3 and C4-2 cell lines using qPCR.

Mechanistic insight into the regulation of P-Rex1 expression is provided by the identification herein of Myc as a regulator of P-Rex1 transcription in prostate CSCs. This finding is relevant because Myc is significantly elevated in prostate CSCs compared to non-CSCs. Also, gene-set enrichment analysis of two independent datasets revealed that Myc expression is associated with tumor cells enriched with an embryonic stem cell-like gene signature. Again without wishing to be bound by theory, the present data also indicated that VEGF/NRP signaling contributes to the regulation of Myc expression and Myc-induction of P-Rex1. This conclusion was supported by the observation that VEGF/VEGFR2 signaling induces Myc expression in breast cancer cells by a mechanism that involves Stat 3. Based on the present data, however, VEGF induction of Myc appeared to be independent of VEGFRs. VEGF/NRP signaling activated focal adhesion kinase (FAK) in CSCs. This observation is interesting because FAK regulates Myc transcription in epidermal stem cells. It is also worth noting that epigenetic repression of P-Rex1 in non-aggressive, prostate cancer cell lines has been observed. However, initial experiments suggested that epigenetic regulation did not account for the marked increase in P-Rex1 mRNA expression in PC3-R cells compared to PC3-S (FIG. 12A).

Figures 12D, 12E, 12F:
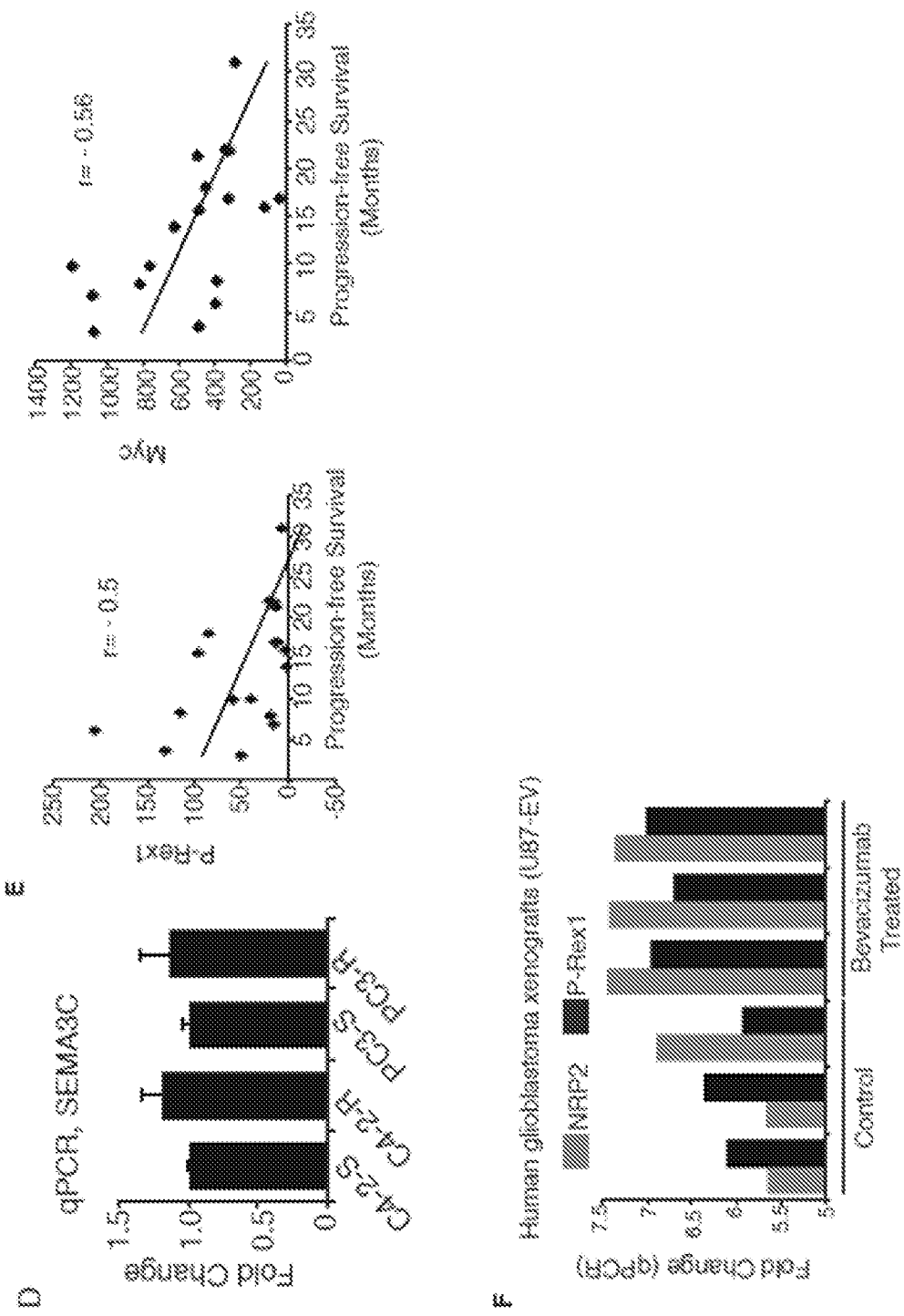
FIG. 12D. The expression of sema-3C was compared in sensitive and resistant PC3 and C4-2 cell lines using qPCR.
FIG. 12E. Correlation of P-Rex1 or Myc expression with progression-free survival was assessed using a published dataset (GSE53127).
FIG. 12F. Gene expression analysis of NRP2 and P-Rex1 was performed using a published dataset (GSE39221).

An important question that arose from the present data is how P-Rex1-mediated Rac1 activation impacted the function of prostate CSCs and promotes resistance to therapy. Without wishing to be bound by theory, P-Rex1/Rac1-mediated ERK activation may sustain the expression of VEGF and NRP2 and the ability of VEGF/NRP2 signaling to enhance the expression of BMI-1 and other stem cell factors. In essence, it is suggested that p-Rex1/Rac1-mediated ERK activation may contribute to a positive feedback loop involving VEGF/NRP2 signaling that sustains stem cell properties in prostate cancer. In addition, VEGF/NRP2 signaling contributes to ERK-mediated induction of Gli1 and BMI-1 expression and that this pathway can feedback to sustain NRP2 expression. Note autocrine semaphorin 3C may promote the survival of glioma stem cells by activating Rac1/nuclear factor-kB signaling (Man, J., Shoemake, J., Zhou, W., Fang, X., Wu, Q., Rizzo, A., Prayson, R., Bao, S., Rich, J. N., and Yu, J. S. 2014. Sema3C Promotes the Survival and Tumorigenicity of Glioma Stem Cells through Rac1 Activation. Cell Rep 9:1812-1826). The expression of semaphorin 3C and targets of nuclear factor-kB signaling was analyzed, and no difference was found between sensitive and resistant populations (FIGS. 12B-12D). Clearly, the available data indicated that Rac1 can affect the function of CSCs by distinct mechanisms that may relate to the biology of specific cancers. It is also worth noting that both semaphorin 3C and VEGF are ligands for NRP2, and an important aspect of the present work is the implication of VEGF-mediated activation of P-Rex1/Rac1 in resistance to bevacizumab, which has significant therapeutic implications. Interestingly, in this context, the present analysis of gene profiling of metastatic colon cancer patients treated with bevacizumab revealed that high P-Rex1 or Myc expression is a significant predictor of poor progression-free survival (FIG. 12E). Also, the analysis of gene expression in human glioblastoma xenografts treated with bevacuzimab indicated increased expression of P-Rex1 and NRP2 (FIG. 12F).

Figures 4A, 4B, 4C, 4D:
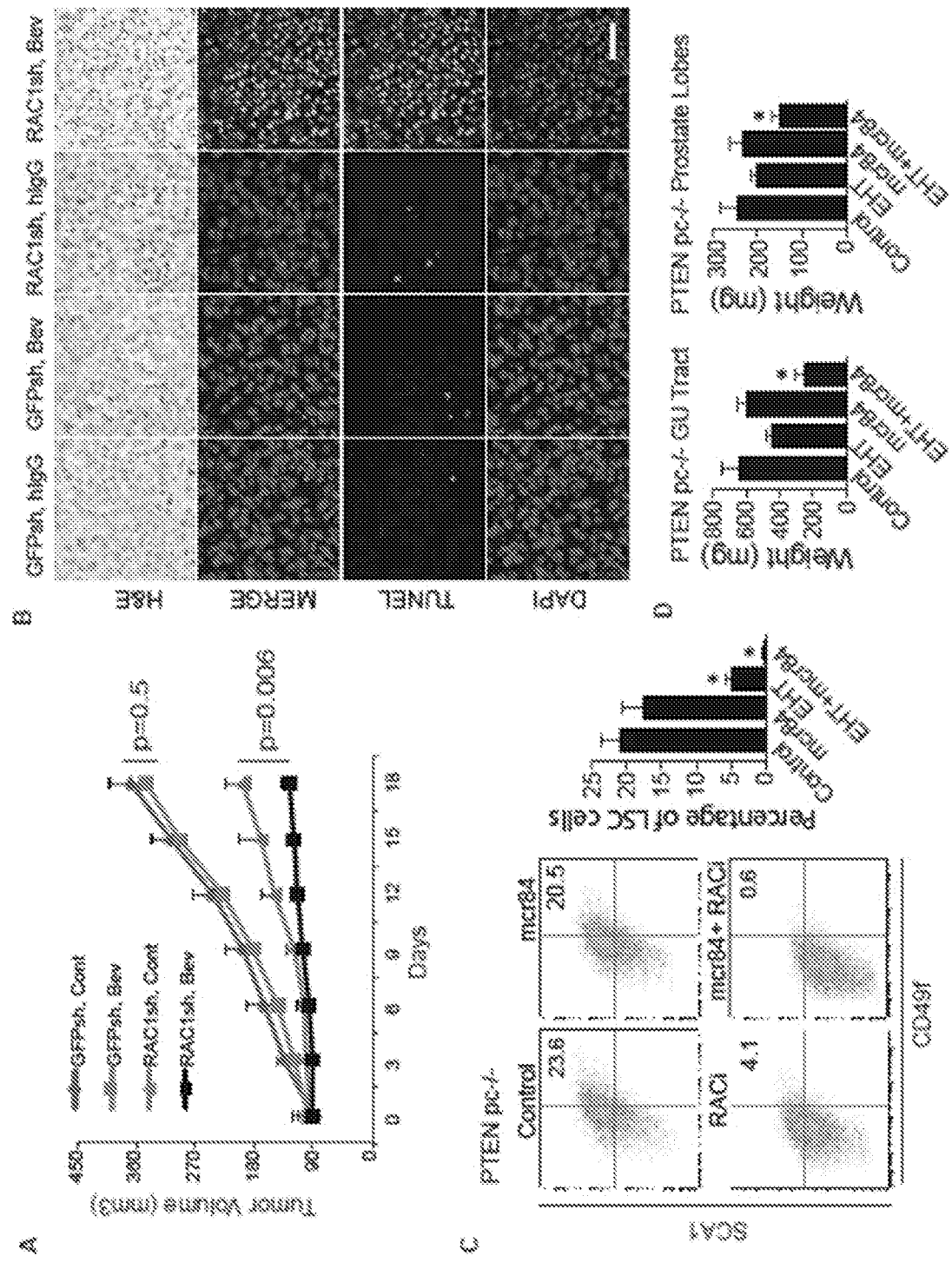
FIGS. 4A-4F. Rac1 inhibition improves sensitivity to VEGF/VEGFR-targeted therapy.

The present data show that efficacy of bevacizumab or VEGFR-targeted therapy in prostate cancer is increased when combined with targeted inhibition of P-Rex1/Rac1. This conclusion is supported by the data presented in FIGS. 4A and 6K. It is also timely and significant because there are few therapeutic options available for men with aggressive prostate cancer, which is enriched with tumor cells with a stem-like phenotype. For example, potent Rac1 inhibitors may reduce the weight of the GU tract in response to EHT1864 (FIG. 4D). Targeting P-Rex1, however, may be desirable. The present data demonstrate that P-Rex1/Rac1 inhibition reduces stem cell properties and renders tumor cells more sensitive to VEGF/VEGFR-targeted therapies.

Treatment

The methods described herein include methods for treating cancer. Generally, the methods include administering a therapeutically effective amount of one or more Rac1 inhibitors or P-Rex1 inhibitors in combination with a VEGF/VEGFR-targeted therapy, as described herein, to a subject who is in need of, or who has been determined to be in need of, such treatment.

As used in this context, to "treat" means to ameliorate at least one symptom of the disorder associated with cancer. Often, cancer is associated with abnormal cell growth with the potential to invade or spread to other parts of the body. Thus, in some embodiments, a treatment can result in death of cancer cells, an inhibition in cell growth or reduce the potential to invade or spread to other parts of the body.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Cancers that can be treated using the methods of the present disclosure include, for example, cancers of the stomach, colon (e.g., colorectal cancer), rectum, mouth/pharynx, esophagus, larynx, liver, pancreas, lung, breast, cervix uteri, corpus uteri, ovary, prostate, testis, bladder, skin, bone, kidney (e.g., renal cell carcinoma), head, neck, and throat, Hodgkins disease, non-Hodgkins leukemia, sarcomas, choriocarcinoma, lymphoma, brain/central nervous system, and neuroblastoma (e.g., pediatric neuroblastoma), among others. One of skill in the art would readily be able to diagnose and select a subject having cancer using methods known in the art.

VEGF/VEGFR-Targeted Therapeutic Agents

Vascular endothelial growth factor (VEGF) was identified and isolated as an endothelial cell-specific mitogen that has the capacity to induce physiological and pathological angiogenesis. In a separate context, a factor that promotes vascular hyperpermeability, initially referred to as "vascular permeability factor," was isolated and later shown to be identical to VEGF. This VEGF is now known as VEGFA and is a member of a larger family of growth factors that also includes VEGFB, VEGFC, VEGFD and placental growth factor (PLGF). These family members differ in their expression pattern, receptor specificity and biological functions. VEGFA, which is often referred to as VEGF, has been studied more than the other members of this family and it has several distinct variants (VEGF121, VEGF145, VEGF148, VEGF165, VEGF183, VEGF189 and VEGF206). These variants occur because of alternative splicing, and they also differ in receptor specificity and function. For a review, see Goel, Hira Lal, and Arthur M. Mercurio. "VEGF targets the tumour cell." Nature Reviews Cancer 13.12 (2013): 871-882.

There are two VEGF receptor (VEGFR) tyrosine kinases (RTKs), Flt-1, known also as VEGFR-1 and KDR, Flk-1, or VEGFR-2. VEGFR-2 is the major mediator of the mitogenic, angiogenic, and permeability-enhancing effects of VEGF. For a detailed review of the biological and signaling properties of the VEGFR, see Ferrara, Napoleone. "Vascular endothelial growth factor: basic science and clinical progress." Endocrine reviews 25.4 (2004): 581-611.

As noted above, the methods described herein include administering an effective amount of a VEGF-targeted therapy to a subject.

In some embodiments, anti-VEGF antibody bevacizumab can be used in the present methods. The antibody bevacizumab and its VEGF-binding activity are reviewed in detail in Ferrara, Napoleone. "Vascular endothelial growth factor: basic science and clinical progress." Endocrine reviews 25.4:581-611 (2004).

Bevacizumab can be administered to a subject, e.g., from 2.5 mg/kg IV to 50 mg/kg IV, for example 5 mg/kg IV, 7.5 mg/kg IV, 10 mg/kg IV, 15 mg/kg IV. In some embodiments, it can be administered to skin or eyes.

It is to be appreciated, however, that the treatment method described herein can also be performed using other anti-VEGF agents (e.g., VEGF or VEGFR inhibitors, such as, but not limited to, other anti-VEGF antibodies, drugs, prodrugs, small molecules, peptides, nucleic acid inhibitors (e.g., siRNA, shRNA, antisense oligonucleotides), fusion proteins, etc.), e.g., as known in the art, that has the ability to inhibit the action of VEGF (e.g., human VEGF) and/or a VEGFR (e.g., VEGFR-1 and/or VEGFR-2) (e.g., human VEGFR-1 or human VEGFR-2) (i.e., to inhibit VEGF signaling). Assays for determining whether an antibody or other agent interferes with VEGF signaling (either by inhibiting VEGF or a VEGFR or the interaction between VEGF and its receptor), for example, are well known in the art, and can be used to determine whether an anti-VEGF agent interferes with VEGF signaling and is therefore encompassed by the presently disclosed methods. Non-limiting examples of such assays include the VEGF inhibition assays described in Foy, Kevin C., et al. "Combined vaccination with HER-2 peptide followed by therapy with VEGF peptide mimics exerts effective anti-tumor and anti-angiogenic effects in vitro and in vivo." Oncoimmunology 1.7 (2012): 1048-1060 and Brekken, Rolf A., et al. "Selective inhibition of vascular endothelial growth factor (VEGF) receptor 2 (KDR/Flk-1) activity by a monoclonal anti-VEGF antibody blocks tumor growth in mice." Cancer research 60.18 (2000): 5117-5124.

By way of non-limiting example, other anti-VEGF antibodies and inhibitors that are known in the art, and, that can be used in the methods disclosed herein include but are not limited to: bevacizumab, ranibizumab, pegaptanib, imatinib, vandetanib, sorafenib, pazopanib, valatanib, vevasiranib, aflibercept, etanercept, anecortave acetate (angiostatic steroid), VEGF-trap (a fusion protein), squalamine lactate, erlotinib, gefitinib (small molecules), Combretastatin A4 Prodrug (an antitubulin/antiangiogenic agent), AdPEDF (Adenovector pigment epithelium-derived factor), Candy (siRNA), protein tyrosine kinase 7 inhibitors (PTK7), lipolytic agents, TG100801, AG013958, AL39324, AGN211745 (VEGF receptor blockers), anti-angiogenic VEGF-A(xxx)b family, VEGF Trap (receptor decoy), protein kinase antibodies to tyrosine kinase inhibitor receptors SIM010603, kinase domain receptor antibodies (KDR1.3 and KDR2.6), GS101 aganirsen (an antisense oligonucleotide against insulin receptor substrate aka IRS-1), picropodophyllin (PPP), tetrameric tripeptide, tissue kallikrein, KH906 (a recombinant human VEGF receptor protein fusion), beta-adreno receptor blocker β3-AR, nicotinic acetycholine receptor antagonists, linomide analogue (Lin05), morpholino oligomers (VEGFR1_MOe13), decursin, prorenin, vasohibin and sirolimus. It will be appreciated that because the amino acids sequences (as well as nucleic acid sequences encoding the amino acid sequences) of VEGF and VEGFRs are known in the art, the skilled artisan can readily design additional anti-VEGF agents for use in the presently disclosed methods.

Dosage ranges for anti-VEGF agents, e.g., those disclosed above, can be readily determined by the ordinarily skilled artisan, and can, e.g., first be determined in animal models for determining dosage, safety and efficacy according to standard methods known in the art.

Rac1 Inhibitors

Rac1, also known as Ras-related C3 botulinum toxin substrate 1, is a signaling G protein (more specifically a GTPase), and is a member of the Rac subfamily of the family Rho family of GTPases. Members of this superfamily appear to regulate a diverse array of cellular events, including the control of cell growth, cytoskeletal reorganization, and the activation of protein kinases.

Rac1 is a pleiotropic regulator of many cellular processes, including the cell cycle, cell-cell adhesion, motility (through the actin network), and of epithelial differentiation (proposed to be necessary for maintaining epidermal stem cells). The sequence of human Rac1 is available in GenBank at Acc. No. NM_006908.4 (mRNA) and NP_008839.2 (protein) (isoform Rac1), or NM 018890.3 (mRNA) and NP_061485.1 (protein) (isoform Rac1b), each of which is incorporated by reference in its entirety.

Provided herein are methods for treating cancer with VEGF/VEGFR-targeted therapy in combination with a Rac1 inhibitor, e.g., a small molecule or inhibitory nucleic acid.

An example of a Rac1 inhibitor includes NSC 23766 described in international patent application WO 2007/016539. The compound is a cell-permeable pyrimidine compound that specifically and reversibly inhibits Rac1 GDP/GTP exchange activity by interfering Rac1 interaction with Rac-specific GEFs.

Another example of a Rac1 inhibitor is EHT 1864 described in international patent application WO 2004/076445. EHT 1864 is a small molecule that blocks the Rac1 signaling pathways.

Other examples of Rac1 inhibitors include those described in EP2433636, WO2007031878, WO2007016539, WO2009007457 and WO2005051392.

Examples of Rac1 inhibitors also include the Rac1 inhibitor W56, sold by Tocris Biosciences (Ellisville, Mo.) or the inhibitors described in Gao, Yuan, et al. "Rational design and characterization of a Rac GTPase-specific small molecule inhibitor." Proceedings of the National Academy of Sciences of the United States of America 101.20 (2004): 7618-7623.

Other examples of Rac1 inhibitors include N4-(9-Ethyl-9H-carbazol-3-yl)-N2-(3-morpholin-4-yl-propyl)-pyrimidine-2,4-diamine (also known as EHop-016), which is described in Montalvo-Ortiz, Brenda L., et al. "Characterization of EHop-016, novel small molecule inhibitor of Rac GTPase." Journal of Biological Chemistry 287.16 (2012): 13228-13238 and US patent application US2013/172552; and F56, which is described in Gao, Yuan, et al. "Trp56 of Rac1 specifies interaction with a subset of guanine nucleotide exchange factors." Journal of Biological Chemistry 276.50 (2001): 47530-47541.

In some embodiments, the Rac1 inhibitor is a selective Rac1 inhibitor. Selective Rac1 inhibitors are compounds that are preferably selective for the Rac1 GTPase as compared with the other Rac GTPase, such as Rac2 or Rac3.

In some embodiments, the P-Rex1 inhibitor is an antibody or antibody fragment that binds specifically to P-Rex1.

Other Rac1 inhibitors are contemplated. For example, Rac1 can be inhibited by various inhibitory nucleic acids, as known in the art or described below. In some embodiments, inhibitory nucleic acids, e.g., shRNA, that target NM_006908.4 (Rac1) or NM_018890.3 (isoform Rac1b) can be used to inhibit Rac1.

P-Rex1 Inhibitors

The Phosphatidylinositol 3,4,5-trisphosphate-dependent Rac exchanger 1 (P-Rex) protein in humans is encoded by the P-Rex1 (or PREX1) gene. P-Rex proteins are Rho/Rac guanine nucleotide exchange factors that participate in the regulation of several cancer-related cellular functions such as proliferation, motility, and invasion. It has been shown to bind to and activate RAC1 by exchanging bound GDP for free GTP. The encoded protein, which is found mainly in the cytoplasm, is activated by phosphatidylinositol-3,4,5-trisphosphate and the beta-gamma subunits of heterotrimeric G proteins. A significant portion of these actions of P-Rex proteins are related to their Rac regulatory properties. The sequence of human P-Rex1 is available in GenBank at NM 020820.3 (mRNA) and NP 065871.2 (protein), each of which is incorporated by reference in its entirety.

Also provided herein are methods for treating cancer with VEGF/VEGFR-targeted therapy in combination with a P-Rex1 inhibitor. In some embodiments, the P-Rex1 inhibitor is a small molecule, an antibody or antibody fragment, or an inhibitory nucleic acid, e.g., a siRNA, a shRNA, an antisense oligonucleotide or a ribozyme. An example of P-Rex1 inhibitor is a shRNA targeting P-Rex1, which is described in van Hooren, K. W., et al. "Phosphatidylinositol-3, 4, 5-triphosphate-dependent Rac exchange factor 1 (PREX1) regulates epinephrine induced exocytosis of Weibel-Palade bodies." J Thromb Haemost 27 (2013), which is incorporated by reference in its entirety. Other P-Rex1 inhibitor are contemplated. For example, P-Rex1 can be inhibited by various inhibitory nucleic acids.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), CRISPR guide sequences, and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA (e.g., Rac1 or P-Rex), i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is preferred but not required, so long as the inhibitory nucleic acids are specific, i.e., they target the intended nucleic acid but do not substantially bind to or affect other nucleic acids.

Routine methods can be used to design an inhibitory nucleic acid that binds to the Rac1 or P-Rex sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within an Rac1 or P-Rex1 sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

It is understood in the art that a complementary nucleic acid sequence need not be 100% complementary to that of its target nucleic acid to be specifically hybridisable. In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA (e.g., Rac1 mRNA or P-Rex mRNA). Thus, oligonucleotides are chosen that are sufficiently complementary to the target, i.e., that hybridize sufficiently well and with sufficient specificity, to give the desired effect.

In some embodiments, the nucleic acid sequence that is complementary to an Rac1 or P-Rex RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets (e.g., Rac1 mRNA or P-Rex mRNA) within the background of cellular RNA. Such a cleavage event renders the RNA non-functional.

CRISPR/Cas9 In some embodiments, the inhibitory nucleic acids act in Clustered Regularly-Interspaced Short Palindromic Repeats (CRISPR) interference (CRISPRi). CRISPRi can sterically repress transcription by blocking transcriptional initiation or elongation. This is accomplished by designing guide RNA, e.g., tracrRNA and crRNA, or single guide RNA (sgRNA), complementary to the promoter or exonic sequences, respectively. The level of transcriptional repression for exonic sequences is strand-specific. sgRNA complementary to the non-template strand more strongly represses transcription compared to sgRNA complementary to the template strand. CRISPR-Cas9 nucleases enable efficient genome editing in a wide variety of organisms and cell types (Sander & Joung, Nat Biotechnol 32, 347-355 (2014); Hsu et al., Cell 157, 1262-1278 (2014); Doudna & Charpentier, Science 346, 1258096 (2014); Barrangou & May, Expert Opin Biol Ther 15, 311-314 (2015)). Target site recognition by Cas9 is programmed by a chimeric single guide RNA (sgRNA) that encodes a sequence complementary to a target protospacer (Jinek et al., Science 337, 816-821 (2012)), but also requires recognition of a short neighboring PAM (Mojica et al., Microbiology 155, 733-740 (2009); Shah et al., RNA Biol 10, 891-899 (2013); Jiang et al., Nat Biotechnol 31, 233-239 (2013); Jinek et al., Science 337, 816-821 (2012); Sternberg et al., Nature 507, 62-67 (2014)).

The CRISPR/Cas9 genome editing system can also be used to inhibit expression of Rac1 and/or P-Rex. A guide RNA (e.g., a single guide RNA, or a paired crRNA/tracrRNA) that binds to a Rac1 and/or P-Rex nucleic acid is administered to or expressed in the cell, along with a CRISPR/Cas9 nuclease. See, e.g., Qi, Lei S., et al. "Repurposing CRISPR as an RNA-guided platform for sequence-specific control of gene expression." Cell 152.5 (2013): 1173-1183; Gilbert, Luke A., et al. "CRISPR-mediated modular RNA-guided regulation of transcription in eukaryotes." Cell 154.2 (2013): 442-451; Jinek et al. Science 337, 816-821 (2012); Jiang et al., Nat. Biotechnol. 31, 233-239 (2013); Hou, Z. et al. Proc. Natl. Acad. Sci. USA 110, 15644-15649 (2013); Mali et al., Science 339, 823-826 (2013); Jinek, M. et al. RNA-programmed genome editing in human cells. Elife 2, e00471 (2013); Horii et al., PeerJ 1, e230 (2013); Shalem, O. et al., Science 343, 84-87 (2014); Sander and Joung, Nature Biotechnology 32, 347-355 (2014). Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556;

US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; US 20150071899; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

CRISPRi can also repress transcription via an effector domain. For example, fusing a repressor domain to a catalytically inactive Cas9, e.g., dCas9, may allow transcription to be further repressed by inducing heterochromatinization. Non-limiting examples of suitable transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. See, e.g., Qi, Lei S., et al. "Repurposing CRISPR as an RNA-guided platform for sequence-specific control of gene expression." Cell 152.5 (2013): 1173-1183; Gilbert, Luke A., et al. "CRISPR-mediated modular RNA-guided regulation of transcription in eukaryotes." Cell 154.2 (2013): 442-451.

Pharmaceutical Compositions

In various embodiments, the disclosure provides pharmaceutical compositions including a pharmaceutically acceptable excipient along with a therapeutically effective amount of the VEGF/VEGFR-targeted therapy, Rac1 inhibitor and/or P-Rex1 inhibitor. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

In various embodiments, the pharmaceutical compositions can be formulated for delivery via any route of administration. "Route of administration" can refer to any administration pathway known in the art, including but not limited to aerosol, nasal, transmucosal, transdermal, or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions can be in the form of solutions or suspensions for infusion or for injection, or as lyophilized powders.

The pharmaceutical compositions can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier can be a liquid or solid tiller, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions can be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic agent (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Administration

The VEGF/VEGFR-targeted therapeutic agents, Rac1 inhibitors, and/or P-Rex1 inhibitors can be delivered to the subject by any suitable delivery route, e.g., injection, infusion, inoculation, direct surgical delivery, or any combination thereof. In some embodiments, VEGF/VEGFR-targeted therapeutic agent, Rac1 inhibitor, and P-Rex1 inhibitor is administered to a subject locally to the site of a tumor, within the tumor, or to an area from which a tumor has been surgically resected.

An appropriate carrier for administering the cells can be selected by one of skill in the art by routine techniques. For example, the pharmaceutical carrier can be a buffered saline solution, liposomes, and nanoparticles etc.

The quantity for administration to a patient and the most convenient route of such administration can be selected using routine methods based upon a variety of factors. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in combination with an overall treatment regimen.

It will be understood that the total daily dosage will be decided by the attending physician within the scope of sound medical judgment. The specific therapeutically effective dose level for any particular subject may depend upon a variety of factors including the disorder being treated and the severity of the disorder; activity of the specific agent employed; the specific pharmaceutical composition employed, the age, body weight, general health, sex and diet of the subject; the time of administration, route of administration, and rate of excretion of the specific inhibitor employed; the duration of the treatment; drugs used in combination or coincidental with the specific inhibitor employed; and like factors well known in the medical arts. For example, it is well within the skill of the art to start doses of the inhibitors at levels lower than those required to achieve the desired therapeutic effect and to gradually increase the dosage until the desired effect is achieved, or to start with a higher dose and later decrease to a maintenance dose.

A Rac1 inhibitor can be administered in combination with a VEGF/VEGFR-targeted therapy, while in some embodiments, only a P-Rex1 inhibitor is administered in combination with a VEGF/VEGFR-targeted therapy. However, in certain situations, both Rac1 inhibitors and P-Rex1 inhibitors can be administered to a subject in combination with a VEGF/VEGFR-targeted therapy to achieve desired effects.

The Rac1 inhibitor and the P-Rex1 inhibitor can be administered before, during, and/or after treatment with a VEGF/VEGFR-targeted therapy. In some embodiments, a Rac1 inhibitor and/or P-Rex1 inhibitor is administered to a patient when (e.g., on the same days, the same weeks, the same hour) the patient is receiving the VEGF/VEGFR-targeted therapy treatment. In some embodiments, Rac1 inhibitors and P-Rex1 inhibitors are administered to a subject with cancer after it is determined that the subject does not respond well to a VEGF/VEGFR-targeted therapy.

Dosage

An "effective amount" is an amount sufficient to effect beneficial or desired results. For example, a therapeutically effective amount is one that achieves the desired therapeutic effect. In some embodiments, an amount of a Rac1 inhibitor and/or P-Rex1 inhibitor administered to a subject who has already developed resistance to VEGF/VEGFR inhibitors can be the same or different from an amount used to prevent development of resistance to VEGF/VEGFR inhibitors. An effective amount can be administered in one or more administrations, applications or dosages. A therapeutically effective amount of a therapeutic compound typically depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

EXAMPLES

The invention is further described in the following examples, which do not limit the scope of the invention described in the claims.

Example 1: P-Rex1 Promotes Resistance to VEGF/VEGFR-Targeted Therapy in Prostate Cancer Materials and Methods The following materials and methods were used in the Examples below.

Cell Lines:

PC3 (ATCC), C4-2 (UroCor) and MyC-CaP were used.

Cell-Based Assays:

The chemosensitivity of prostate cancer cells was determined using a standard 3-(4,5-dimethylthiazol-2-yl)-2,5-diphenyltetrazolium bromide (MTT) cytotoxicity assay. The assay was performed 72 hours after treatment. FACS was used to isolate cells based on their surface expression of CD44, CD24, and the α6 and β4 integrins. The detailed procedure for isolating LSC cells from PTEN$^{pc-/-}$ mice using lineage markers (CD31, CD45, and Ter119), Sca-1, and CD49f is described, e.g., in Mulholland, D. J., Xin, L., Morim, A., Lawson, D., Witte, O., and Wu, H. 2009. Lin-Sca-1+CD49fhigh stem/progenitors are tumor-initiating cells in the Pten-null prostate cancer model. Cancer Res 69:8555-8562; Lawson, D. A., Xin, L., Lukacs, R. U., Cheng, D., and Witte, O. N. 2007. Isolation and functional characterization of murine prostate stem cells. Proc Natl Acad Sci USA 104:181-186.

Isolation of Human Prostate Tumor Cells and Laser Capture Microscopy (LCM):

Human prostate tumor tissue was obtained from UMASS Cancer Center Tissue Bank in compliance with the Institutional Review Board of the University of Massachusetts Medical School. The discarded but freshly resected, prostate tumors were digested with collagenase at 37° C. and epithelial cells were isolated using an EpCaM antibody. Frozen sections were microdissected by laser capture microscopy (Arcturus PixCell 2) to obtain pure populations of tumor cells of defined Gleason grades. RNA was isolated from these microdissected samples using the RNeasy kit (Qiagen) and cDNA was prepared using Superscript II reverse transcriptase (Invitrogen). Quantitative real-time PCR was done using the Taqman assay kit (Applied Biosystems). Typical methods were described in, e.g., Goel, H. L., Chang, C., Pursell, B., Leav, I., Lyle, S., Xi, H. S., Hsieh, C. C., Adisetiyo, H., Roy-Burman, P., Coleman, I. M., et al. 2012. VEGF/Neuropilin-2 Regulation of Bmi-1 and Consequent Repression of IGF-1R Define a Novel Mechanism of Aggressive Prostate Cancer, Cancer Discovery 2:906-921.

Promoter Activity and ChIP Assays:

Prostate cancer cells were transfected with the P-Rex1 promoter luciferase construct (−2021/+3) and Renilla luciferase construct to normalize for transfection efficiency. Relative light units were calculated upon normalization with Renilla luciferase activity. ChIP assays were performed. Typical methods were described, e.g., in Goel, H. L., Chang, C., Pursell, B., Leav, I., Lyle, S., Xi, H. S., Hsieh, C. C., Adisetiyo, H., Roy-Burman, P., Coleman, I. M., et al. 2012. VEGF/Neuropilin-2 Regulation of Bmi-1 and Consequent Repression of IGF-1R Define a Novel Mechanism of Aggressive Prostate Cancer, Cancer Discovery 2:906-921. All ChIP experiments were repeated at least two times. The sequences of primers used to amplify the P-Rex1 promoter are provided below.

Statistics:

Unless otherwise cited, all values are presented as the mean±SD. For student's t-test, comparisons between two groups were performed using two-tailed, assuming equal variance among groups. P value less than 0.05 was considered significant. The correlation of Myc and P-Rex1 expression in human prostate cancer specimens was done using kappa statistics. The kappa estimate was tested against a null hypothesis of Kappa=0.0. For tumor-free survival xenograft experiments, the comparison between two curves were done using Log-rank (Mantel-Cox) test. All experiments in this disclosure were repeated at least twice with the exception of experiments involving the culture of primary tumor cells, and data from one representative experiment is shown.

Primers:

The sequence of primers used to amplify the P-Rex1 promoter are:

```
Primer Set 1, P1: Amplicon Size = 140; -1954/-1814
For:    GTTACCCTGCCAGTTGGATT     (SEQ ID NO: 1)

Rev:    TACCTTTCTGAGCCTCCGTT     (SEQ ID NO: 2)

Primer Set 2, P2: Amplicon Size = 88, -1641/-1553
For:    AAGGCCCAGATCAAATGCTA     (SEQ ID NO: 3)

Rev:    AGGACACAGGGAGAGAATGG     (SEQ ID NO: 4)

Primer Set 3, P3: Amplicon Size = 116, -1174/-1058
For:    ACCATGATCGTTCCCGTTAT     (SEQ ID NO: 5)

Rev:    GTCAGCTGCTCAGGTTCAAA     (SEQ ID NO: 6)

Primer Set 4, P4: Amplicon Size = 71 -792/--720
For:    GAAAGGAAACGGGAAAGAGA     (SEQ ID NO: 7)

Rev:    CTACCACGACCTTGGGAAG      (SEQ ID NO: 8)

Primer Set 5, P5: Amplicon Size = 149 -548/-399
For:    TTTACTTGGCCCGAGCAG       (SEQ ID NO: 9)

Rev:    GAACCGAGCGTACCAACTC      (SEQ ID NO: 10)
```

Cells with Stem-Like Properties are Resistant to Anti-VEGF/VEGFR Therapies

Figure 1B:
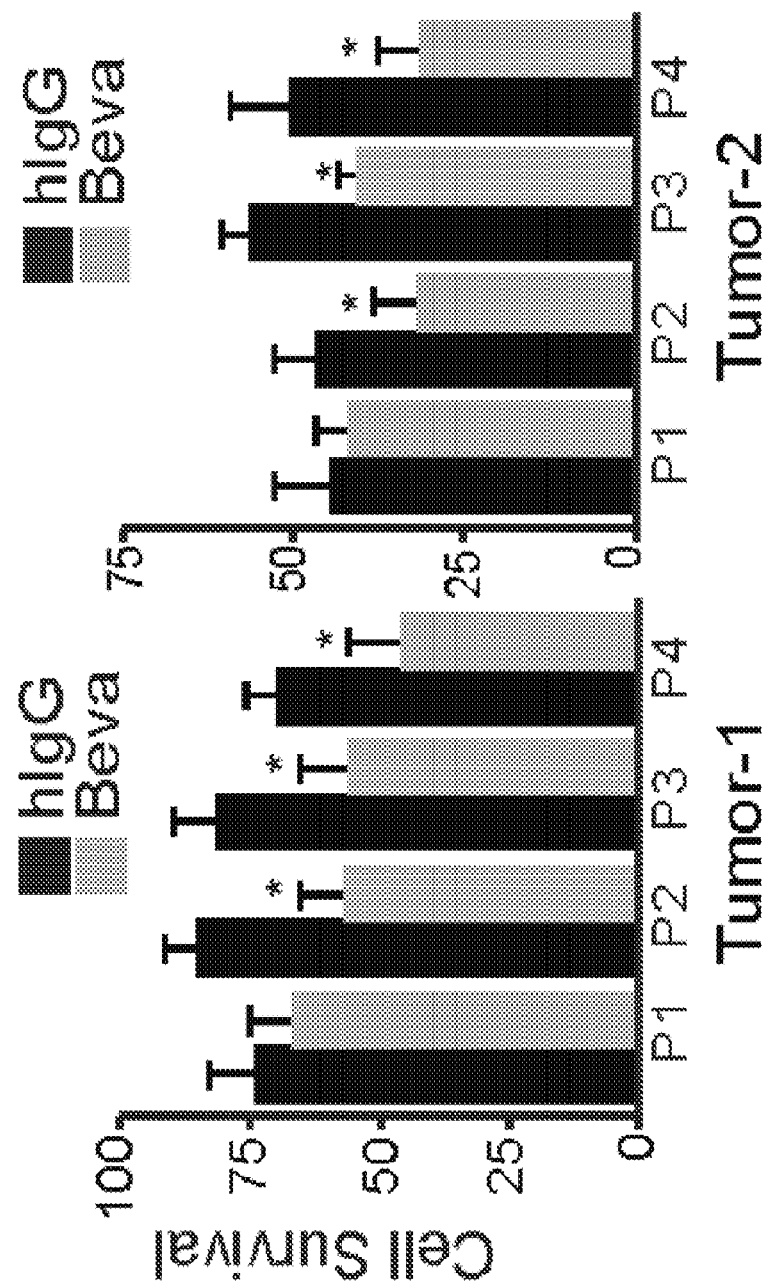
Figure 1C:
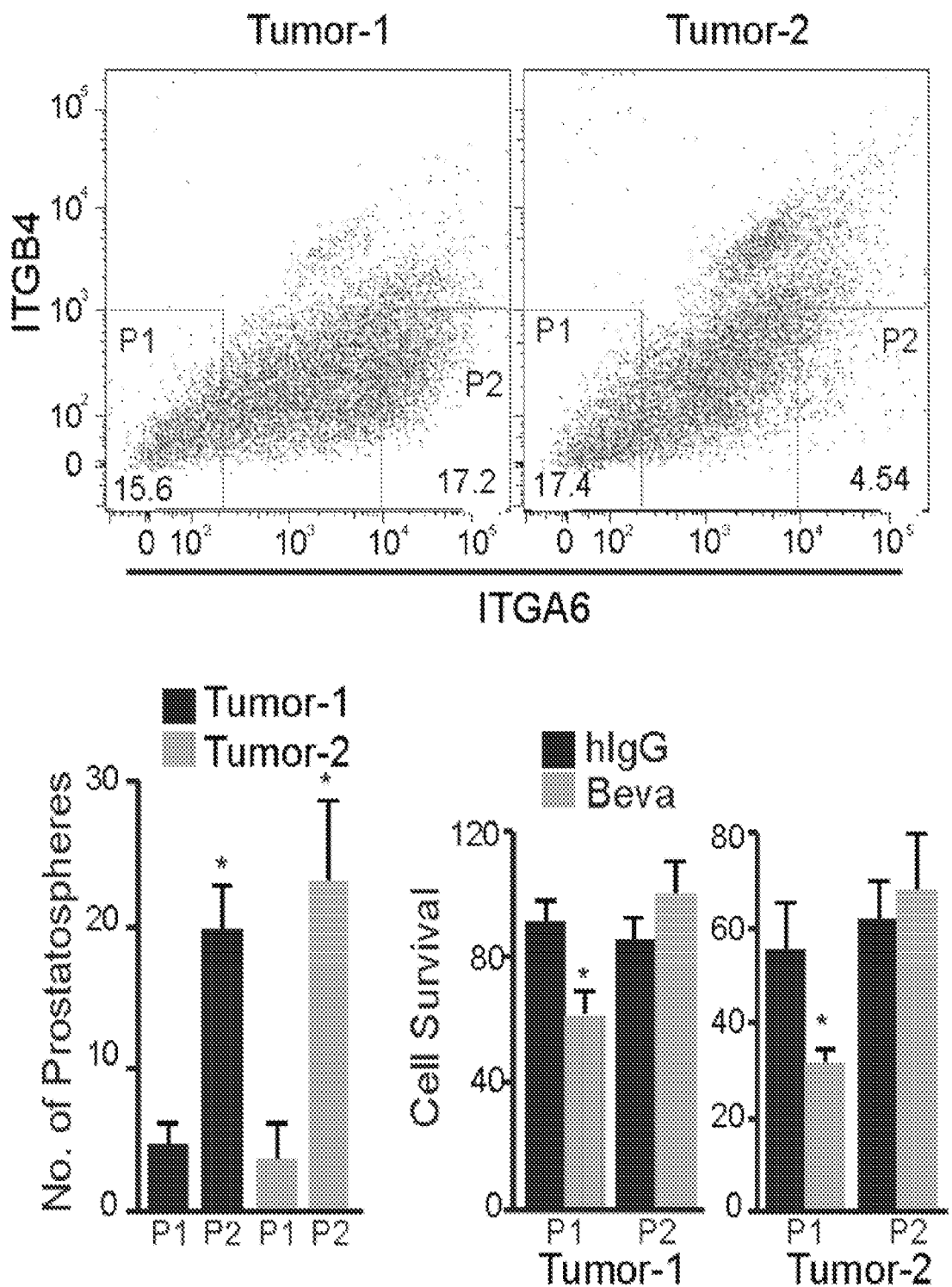

To assess the sensitivity of prostate CSCs to anti-VEGF therapy, we isolated a CD44$^+$CD24$^-$population from two freshly harvested, human prostate tumors. This population is enriched for progenitor/stem cell. Indeed, the CD44$^+$CD24$^-$ (P1) sub-population isolated from these tumors formed significantly more prostatospheres than the other sub-populations (FIG. 1A) and it is the only subpopulation that exhibited resistance to bevacizumab (Beva) treatment (FIG. 1B). We also sorted these prostate tumors based on expression of CD49f (a6 integrin), another stem cell marker, and observed that the high CD49f population formed significantly more prostatospheres and exhibited resistance to bevacizumab treatment compared to the low CD49f population (FIG. 1C).

To understand the mechanism behind the resistance of CSCs to bevacuzimab, we exposed prostate cancer cell lines (PC3 and C4-2) to increasing concentrations of bevacizumab until this inhibitor no longer affected their survival (~6 months). To circumvent VEGF-independent or transactivation of VEGF tyrosine kinase receptors (VEGFRs), we subsequently exposed these cells to increasing concentrations of sunitinib, an inhibitor of VEGRs and other receptor tyrosine kinases, along with bevacizumab. However, sunitinib did not have a significant effect on bevacizumab-resistant cells. The resistant cell lines generated are referred to as PC3-R and C4-2R. As controls, we also exposed these cell lines to control IgG (hIgG) and DMSO and refer to these as sensitive cell lines (PC3-S and C4-2S) (FIGS. 1D-1E).

Figures 1D, 1E, 1F, 1G, 1H:
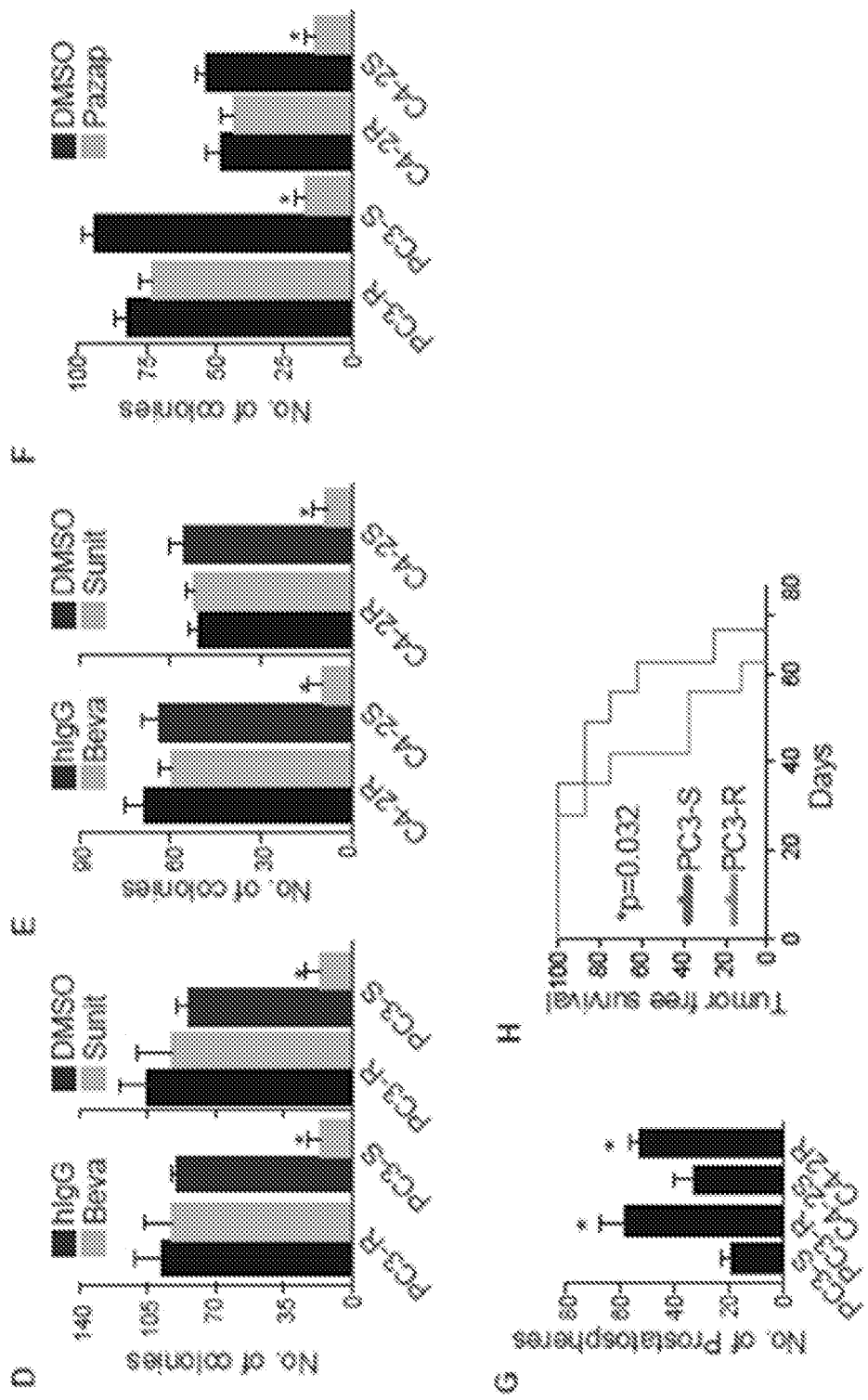
Figures 8A, 8B:
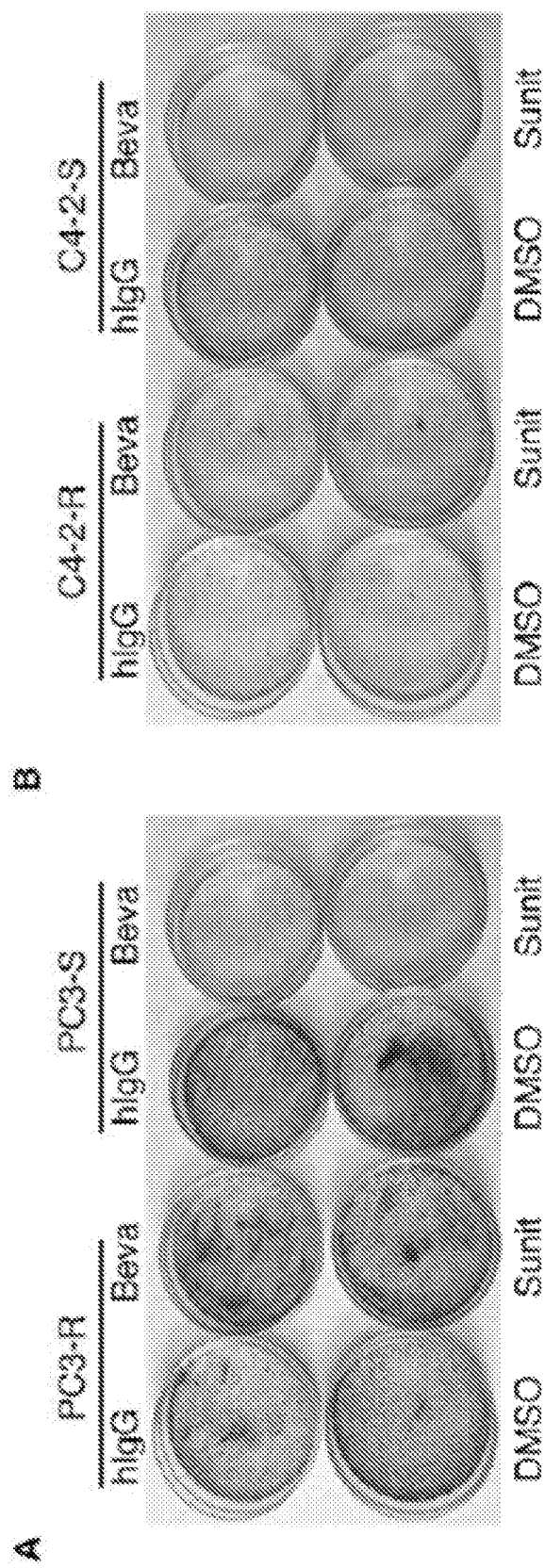
FIGS. 8A-F. Effect of VEGF-targeted therapy on sensitive and resistant cell lines.
Figures 8C, 8D, 8E, 8F:
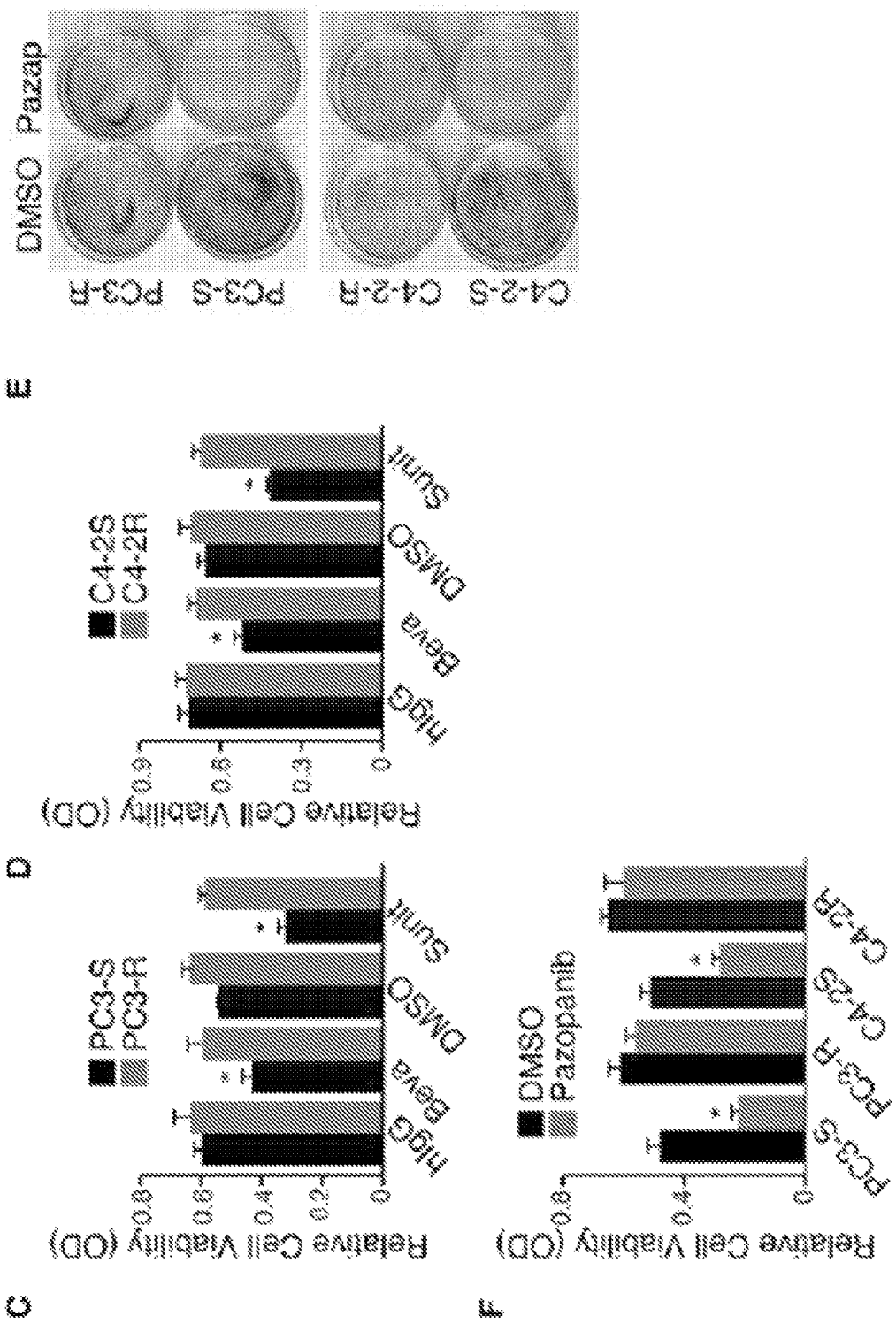

Neither bevacizumab nor sunitinib inhibited the ability of the resistant cell lines to form colonies or survive, in contrast to the sensitive cell lines (FIGS. 1D-1E; FIGS. 8A-8D). Interestingly, PC3-R and C4-2R cells are also resistant to pazopanib, another VEGFR inhibitor (FIG. 1F; FIGS. 8E-8F), confirming the pathway specificity of the observed resistance. The resistant cell lines we generated are enriched for stem cell properties based on the fact that they were able to form prostatospheres and initiate tumors in NSG mice to a significantly greater extent than the sensitive cells (FIGS. 1G-1H).

Figures 2A, 2B, 2C, 2D, 2E, 2F:
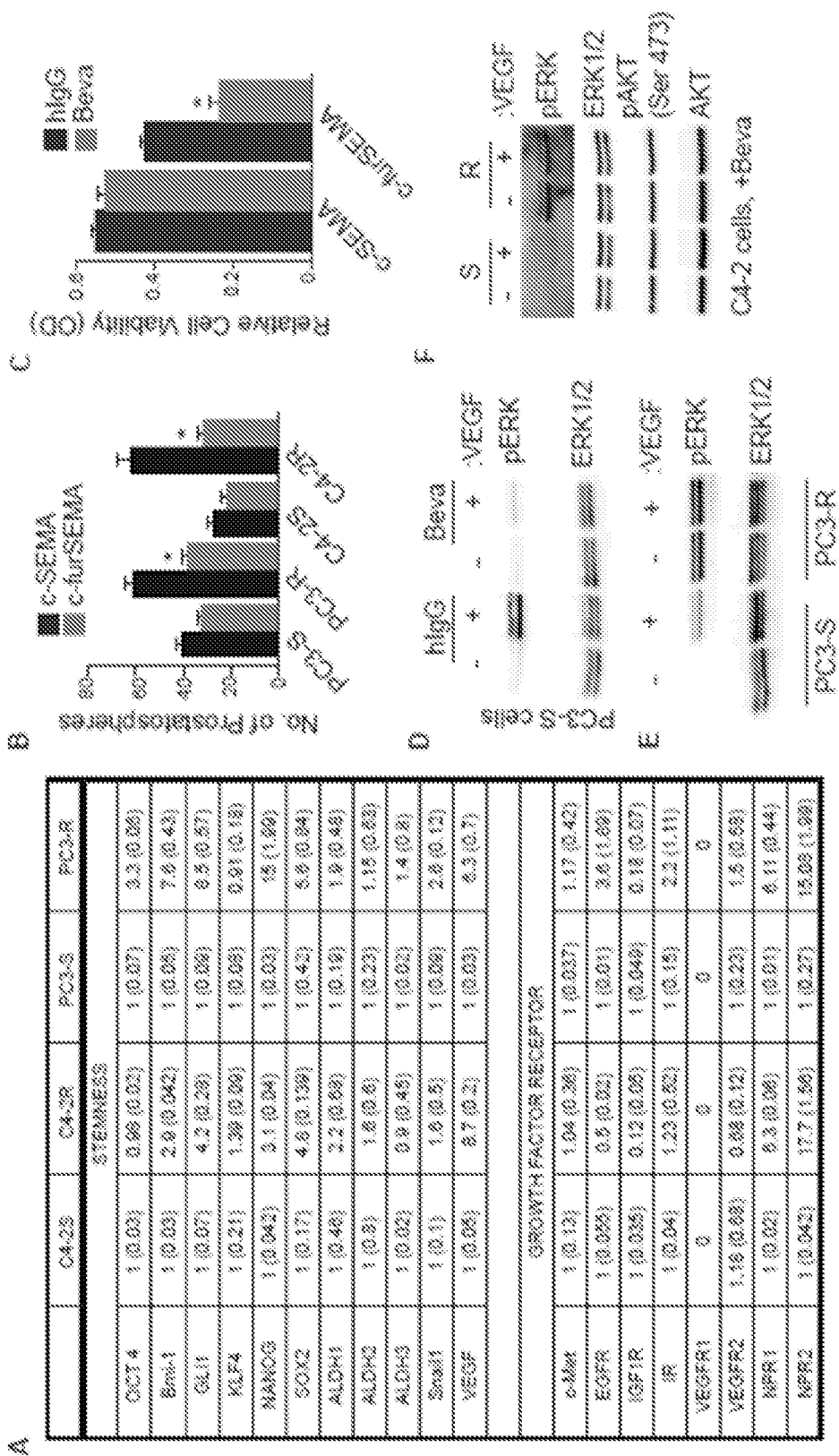
FIGS. 2A-2N. VEGF/NRP-mediated activation of ERK promotes resistance to therapy.
FIG. 2B. Resistant and sensitive populations were analyzed for prostatosphere formation in the presence of either a NRP inhibitory peptide (c-furSEMA) or control peptide (c-SEMA).
FIG. 2C. Resistant and sensitive populations were analyzed for sensitivity to bevacuzimab (1 mg/ml) in the presence of either a NRP inhibitory peptide (c-furSEMA) or control peptide (c-SEMA).
FIG. 2D. PC3-S cells were serum-deprived overnight and stimulated with VEGF (50 ng/ml) for 30 minutes in the presence or absence of bevacuzimab (5 mg/ml). The activation of ERK was analyzed by immunoblotting using a phospho-specific antibody.
FIG. 2E. PC3 sensitive or resistant cells were serum-deprived overnight and stimulated with VEGF (50 ng/ml) for 30 minutes. The activation of ERK was analyzed by immunoblotting using a phospho-specific antibody.
FIG. 2F. Sensitive and resistant C4-2 cell lines were serum-deprived overnight and stimulated with VEGF (50 ng/ml) for 30 minutes in the presence of bevacuzimab (5 mg/ml). The activation of ERK and AKT was analyzed by immunoblotting using phospho-specific antibodies.
Figures 9A, 9B, 9C, 9D, 9E:
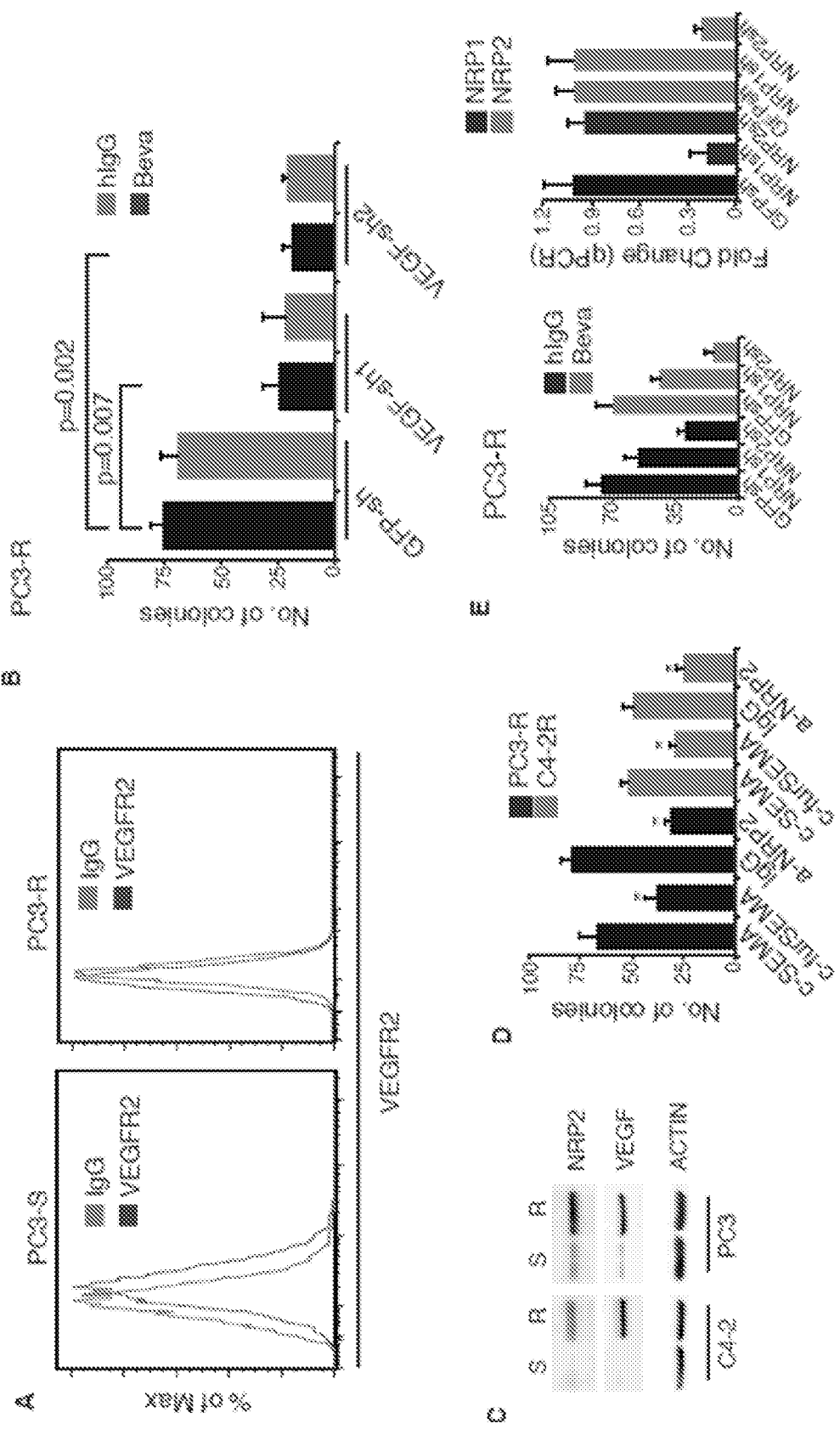
FIGS. 9A-H. Resistant cell lines lack surface expression of VEGFR2.

Neuropilin-Mediated Rac1 Activation Promotes Resistance to VEGF/VEGFR-Targeted Therapy We compared the expression of key stem cell genes between the sensitive and resistant cell lines to substantiate our hypothesis that resistant cells exhibit stem cell properties. Indeed, the resistant cell lines are enriched in the expression of genes associated with CSCs (Nanog, Sox2, BMI1, ALDH1) compared to the sensitive cell lines (FIG. 2A). Interestingly, VEGF expression is markedly elevated in the resistant cell lines despite the fact that these cells were selected based on their resistance to bevacizumab. In contrast, no significant difference was observed in VEGFR2 expression between sensitive and resistant cells, and these cells lack expression of VEGFR1 (FIG. 2A). Down-regulation of VEGF expression in resistant cells reduced their ability to form colonies, suggesting that VEGF signaling contributes to bevacizumab and sunitinib resistance in a VEGFR2-independent manner (FIGS. 9A-9B). The nature of this signaling was indicated by the observation that Neuropilin (NRP) expression, especially NRP2, is dramatically elevated in resistant cell lines (FIG. 2A and FIG. 9C). These expression data raised the possibility that VEGF/NRP signaling is responsible for resistance to bevacuzimab and sunitinib, especially given the fact that bevacuzimab blocks the interaction of VEGF with VEGF tyrosine kinase receptors (VEGFR1-3), but not with NRPs. The observation that IGF-1R expression is reduced dramatically in resistant cells (FIG. 2A) is consistent with the finding that VEGF/NRP2 signaling represses IGF-1R transcription.

Figures 9F, 9G, 9H:
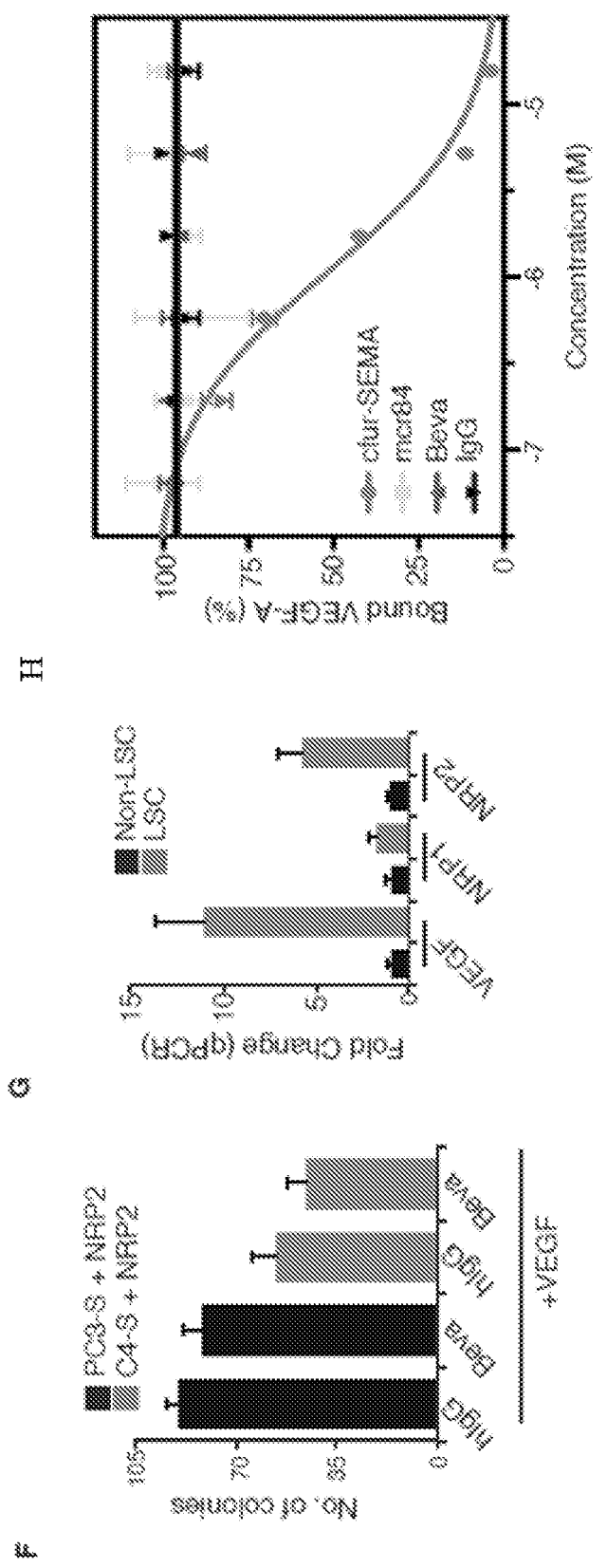

The contribution of NRPs to resistance was investigated using c-furSEMA, an inhibitory peptide, which blocks interactions of VEGF with NRPs. This peptide inhibited formation of prostatospheres in resistant cell lines and showed no effect in sensitive cells (FIG. 2B). Importantly, treatment with c-furSEMA or an inhibitory NRP2 antibody decreased colony formation, highlighting a critical role for NRPs in the survival of resistant cells (FIG. 9D). We also observed that inhibition of VEGF-NRP binding using c-furSEMA increased the sensitivity of resistant cells to bevacizumab, substantiating the critical function of NRPs in resistance to this VEGF inhibitor (FIG. 2C). Furthermore, down-regulation of either NRP2 or NRP1 significantly reduced colony formation and increased sensitivity to bevacizumab (FIG. 9E). We focused on NRP2 for subsequent experiments based on the observation that NRP2 down-regulation had a more potent inhibitory effect on colony formation than NRP1 (FIG. 9E). Ectopic expression of NRP2 in sensitive cells induces resistance to bevacizumab in the presence of VEGF, directly implicating NRP2 in resistance to bevacizumab (FIG. 9F).

Figures 2G, 2H, 2I, 2J, 2K, 2L, 2M, 2N:
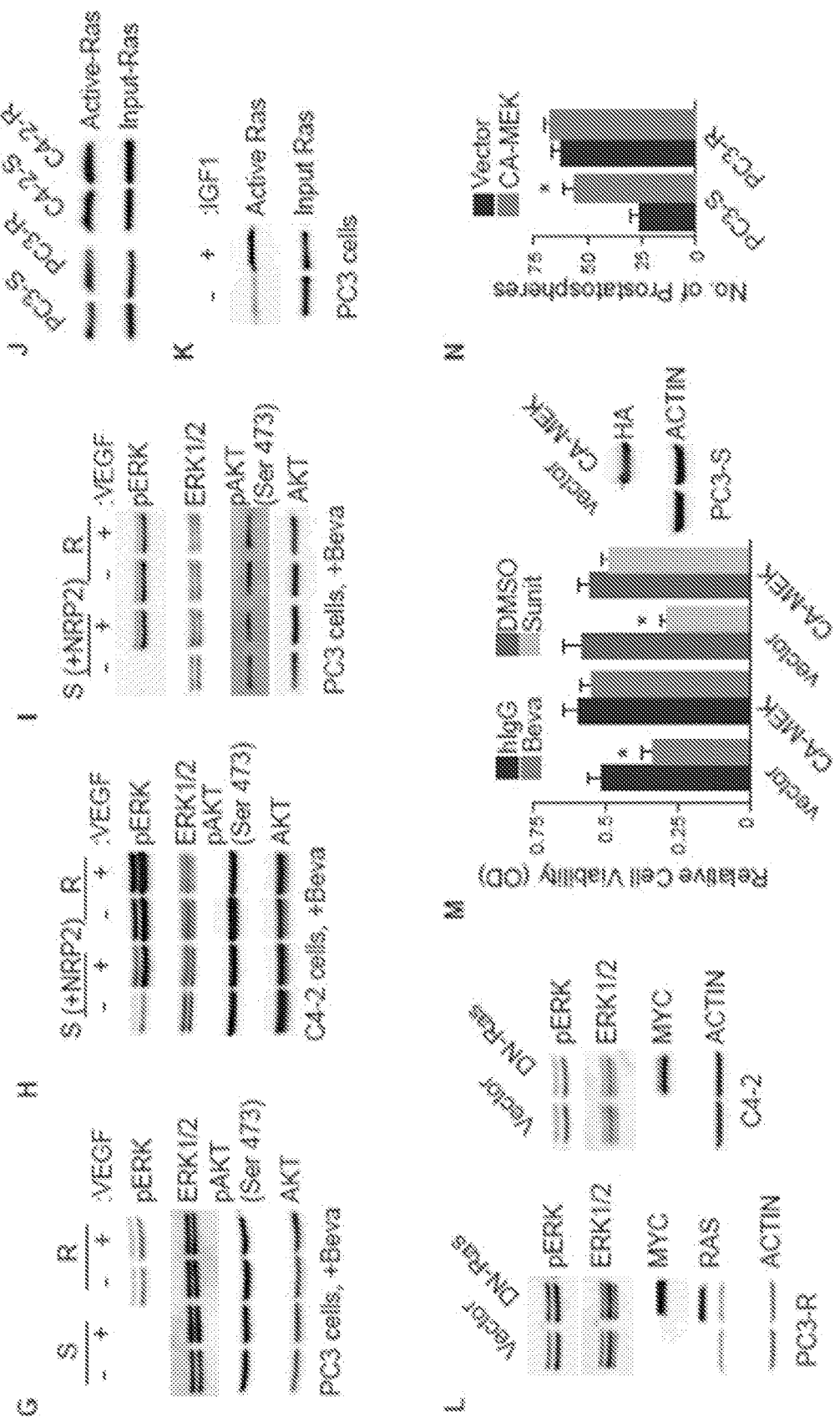
FIG. 2G. Sensitive and resistant PC3 cell lines were serum-deprived overnight and stimulated with VEGF (50 ng/ml) for 30 minutes in the presence of bevacuzimab (5 mg/ml). The activation of ERK and AKT was analyzed by immunoblotting using phospho-specific antibodies.
FIG. 2H. NRP2 was expressed in sensitive populations of C4-2 cells. These cells and resistant C4-2 cells serum-deprived overnight and stimulated with VEGF (50 ng/ml) for 30 minutes in the presence of bevacuzimab (5 mg/ml). The activation of ERK and AKT was analyzed by immunoblotting.
FIG. 2I. NRP2 was expressed in sensitive populations of PC3 cells. These cells and resistant PC3 cells serum-deprived overnight and stimulated with VEGF (50 ng/ml) for 30 minutes in the presence of bevacuzimab (5 mg/ml). The activation of ERK and AKT was analyzed by immunoblotting.
FIG. 2J. Ras activation was analyzed in sensitive and resistant PC3 and C4-2 cell using the Raf1 binding assay.
FIG. 2K. PC3-S cells were stimulated with IGF-1 (100 ng/ml) for 20 minutes and Ras activation was analyzed.
FIG. 2L. Resistant PC3 and C4-2 cells were transfected with a Myc-tagged dominant-negative (DN) Ras construct and ERK activation was analyzed by immunoblotting.
FIG. 2M. Sensitive PC3 cells were transfected with an HA-tagged, constitutively-active (CA) MEK construct, and sensitivity to bevacuzimab was analyzed.

Based on our finding that VEGF/NRP signaling promotes resistance to VEGF/VEGFR-targeted therapy, we investigated the details of this signaling mechanism. Initially, we compared activation of AKT and ERK in sensitive and resistant cell lines, in the absence or presence of exogenous VEGF. Sensitive cell exhibited increased ERK activation in response to VEGF, which was inhibited by bevacizumab (FIG. 2D). In contrast, resistant cells displayed relatively high ERK activation even in the absence of exogenous VEGF (FIG. 2E), presumably the consequence of autocrine VEGF secretion in these cells. Interestingly, bevacizumab was unable to inhibit ERK activation in resistant cells (FIGS. 2F-2G), suggesting that VEGF can induce ERK activation in these cells independently of VEGFR. No differences in AKT activation were observed between sensitive and resistant cells (FIGS. 2F-2G). Since bevacizumab does not block the interaction of VEGF with NRP, we expressed NRP2 in sensitive cells and observed that it induced ERK activation in the presence of bevacizumab (FIGS. 2H-2I). This result implicates VEGF/NRP2 signaling in ERK activation. Interestingly, RAS does not appear to be involved in this mode of ERK activation based on the findings that no differences in the levels of active RAS were detected between sensitive and resistant cells (FIGS. 2J-2K), and that expression of a dominant-negative RAS (DN-RAS) did not alter ERK activation in resistant cells (FIG. 2L). ERK activation contributes to resistance based on the finding that expression of constitutively active MEK in sensitive cells increased their resistance to bevacizumab and sunitinib-mediated inhibition of viability and prostatosphere formation (FIGS. 2M-2N).

Figures 3A, 3B, 3C, 3D, 3E, 3F:
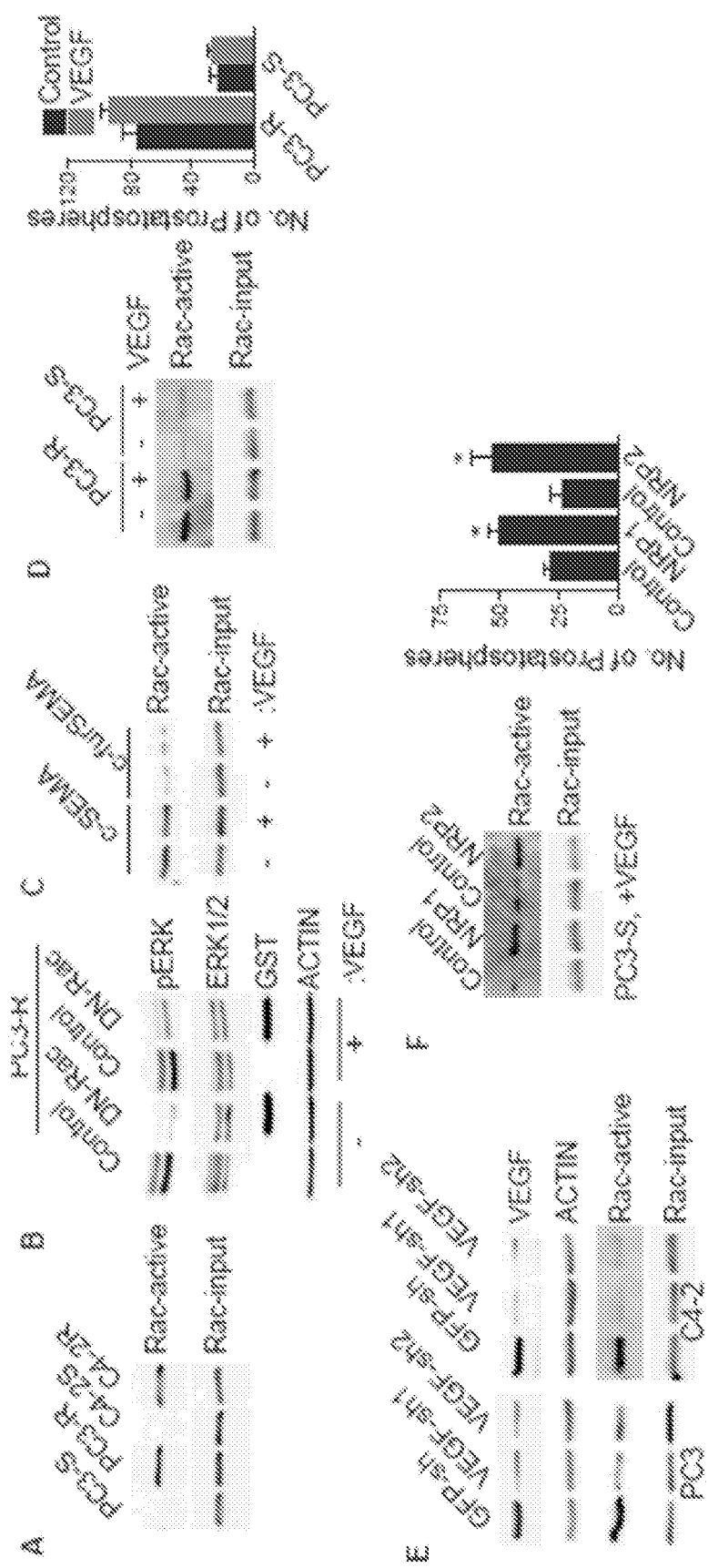
FIGS. 3A-3J. Rac1 mediates of stem cell properties and resistance to VEGF/VEGFR-targeted therapy.

Subsequently, we focused on Rac1 as a mediator of Ras-independent ERK activation based on that Rac1 is a major effector of NRP/plexin signaling and plays a central role in vascular development in response to VEGF. Also, activation of Rac1 is associated with aggressive prostate cancer and Rac1$^{-/-}$ mice exhibit impaired ERK activation and regression of hematopoietic stem cells. Indeed, we found that resistant cell lines exhibit robust Rac1 activation compared to sensitive cells (FIG. 3A). Rac1 mediates ERK activation in resistant cells based on the use of a dominant negative Rac construct (FIG. 3B). The activity of Rac1 in resistant cells is dependent upon NRP signaling because c-furSEMA reduced Rac1 activity significantly (FIG. 3C). In contrast, addition of recombinant VEGF did not increase Rac1 activity or the ability of these cells to make prostatospheres (FIG. 3D), most likely because resistant cells express high levels of autocrine VEGF (FIG. 2A). This possibility was confirmed by depleting VEGF expression in these cells and observing a marked reduction in Rac1 activity (FIG. 3E).

Figures 3G, 3H, 3I, 3J:
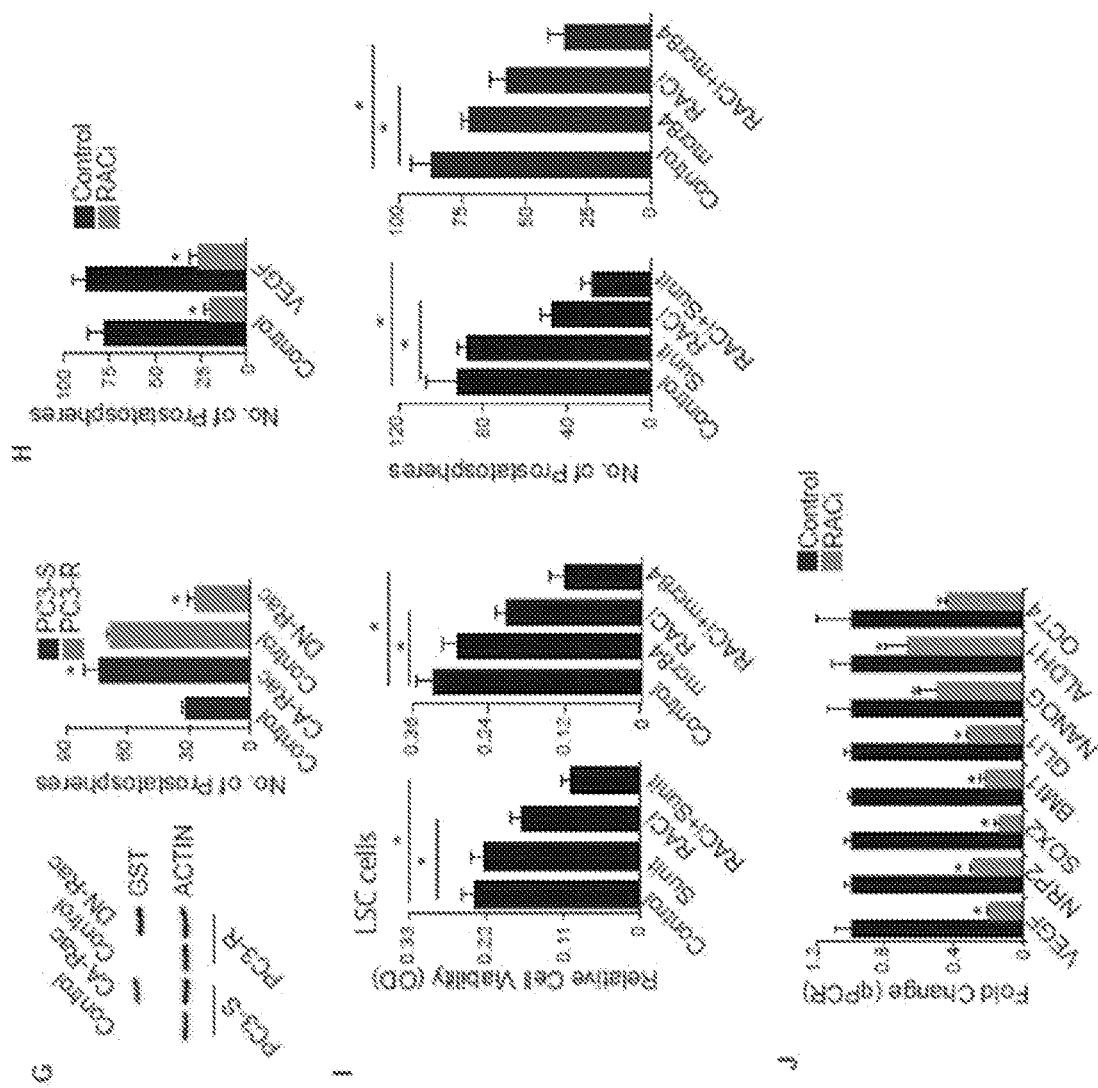

Sensitive cells may not respond to VEGF and activate Rac1 because they lack significant NRP expression. To test this possibility, we expressed either NRP1 or NRP2 in these cells and observed an increase in Rac1 activity and prostatosphere formation (FIG. 3F). Also, expression of a constitutively active Rac1 in sensitive cells increased prostatosphere formation and expression of a dominant negative Rac1 in resistant cells decreased their formation (FIG. 3G). These results were confirmed using a Rac1 inhibitor (EHT1864) in resistant cells, which reduced the number of prostatospheres (FIG. 3H). Although there is some indication that the ability of EHT1864 to inhibit Rac1 may be indirect, we conclude from the use of dominant negative and constitutively active Rac1 constructs, as well as EHT1864, that Rac1 is the primary mediator of VEGF/NRP-mediated prostatosphere formation.

To validate the role of Rac1 in tumor initiation, we utilized the PTEN$^{pc-/-}$ transgenic mouse model of prostate cancer. Tumors that form in this model harbor a small population of tumor initiating cells defined as Lin$^-$Sca$^+$CD49f$^{high}$ (referred to as LSC cells). We purified these LSC cells from 10 week old PTEN$^{pc-/-}$ mice and observed increased expression of VEGF and NRP2 in this population compared to non-LSC cells (FIG. 9G). We tested the hypothesis that Rac inhibition increases sensitivity to mcr84, which recognizes both mouse and human VEGF, and sunitinib. This antibody (mcr84) does not inhibit the interaction of VEGF with NRPs (FIG. 9H). Consistent with our hypothesis, we observed that the Rac1 inhibitor increased the sensitivity of LSC cells to these drugs (FIG. 3I). Inhibition of Rac1 also reduced the expression of VEGF, NRP2 and other sternness-related genes (FIG. 3J).

Figures 4E, 4F:
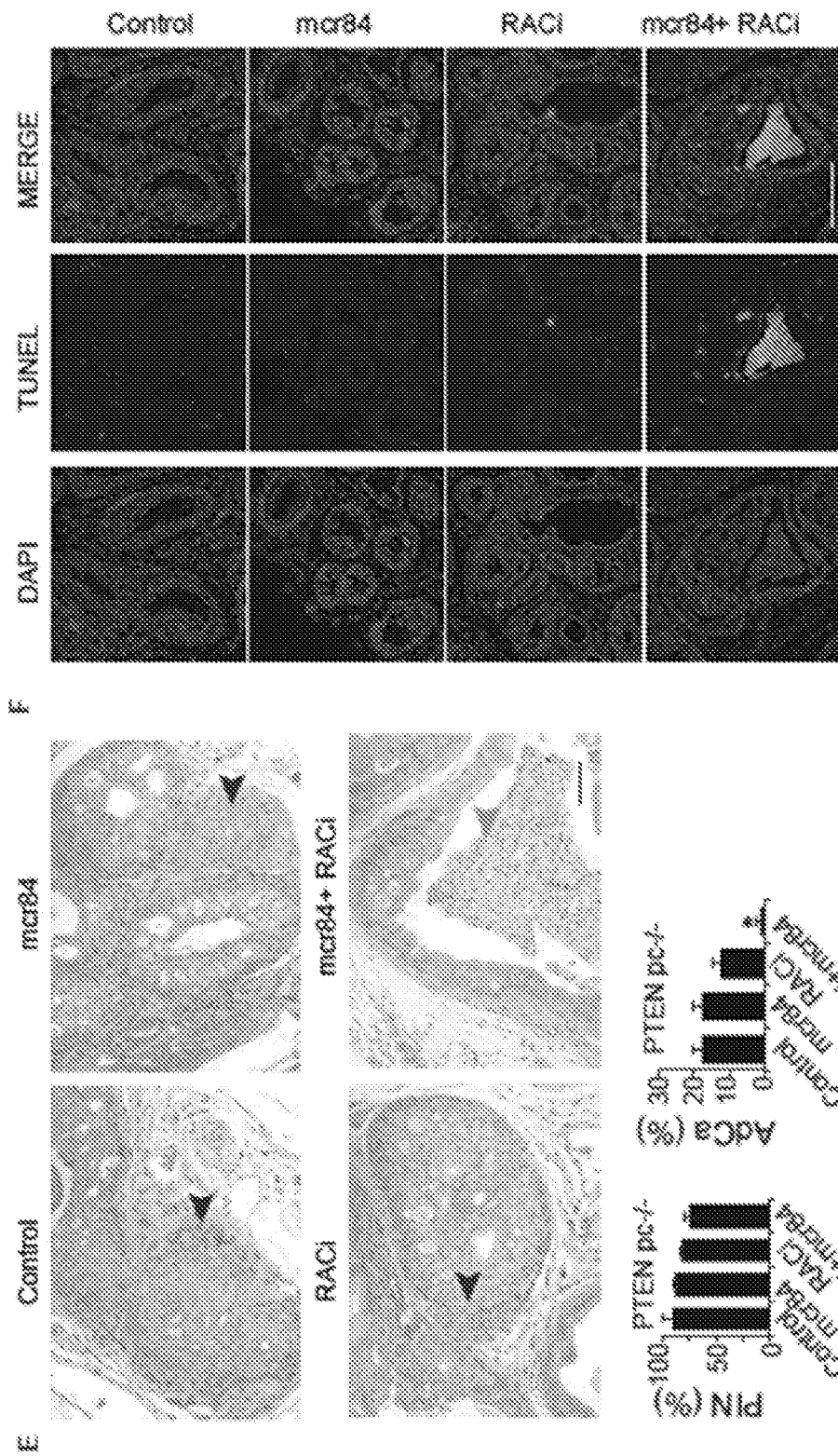

The data in FIG. 3I suggest that the response to VEGF/VEGFR-targeted therapy (bevacizumab or mcr84) would be improved significantly if Rac1 expression or activation were inhibited. To test this possibility initially, we treated control and Rac1-depleted PC3-R xenografts with bevacizumab or vehicle. Bevacizumab treatment alone had no significant effect on tumor growth validating our in vitro finding that resistant cell lines can tolerate bevacizumab treatment. Although Rac1 inhibition reduced tumor volume, the combination of bevacizumab and Rac1 depletion resulted in a significantly better decrease in tumor volume (FIG. 4A). Moreover, the residual tumors harvested from mice that received the combined treatment contained mostly apoptotic cells, in contrast to either bevacizumab treatment or Rac1 inhibition alone (FIG. 4B). This unexpected observation suggests that resistant cells acquire sensitivity to bevacizumab as a result of Rac1 inhibition. Presumably, Rac1 inhibition alone reduces tumor growth but does not induce the massive apoptosis seen with combined treatment. To pursue this hypothesis further, PTEN$^{pc-/-}$ transgenic mice were treated with the Rac1 inhibitor (EHT1864), mcr84 or both at the start of puberty (6 weeks). Indeed, Rac1 inhibition reduced the number of LSC cells significantly but the combined treatment abolished the LSC population. We also compared the impact of mono- and combined therapy on PTEN$^{pc-/-}$ tumors by calculating the weights of the isolated GU tracts and prostate lobes. Combined treatment (EHT1864+mcr84) resulted in a significant decrease in the weight of the isolated GU tracts and prostate lobes compared to either EHT1864 or mcr84 alone (FIGS. 4C-4D). Pathological examination revealed that tumors progressed to well-differentiated adenocarcinomas in mice that received either control or single agent treatment. Interestingly, however, PIN lesions were observed in the prostate glands of mice that received combined treatment (RACi+mcr84), suggesting a delay in tumor progression as a result of the reduced number of LSC cells (FIG. 4E). Moreover, a mass of cells in the lumen of the gland was evident in mice that received the combined treatment. Further analysis using the TUNEL assay demonstrated that this mass of cells is apoptotic, indicating that combined treatment can induce apoptotic cell death within PIN lesions (FIG. 4F). These tumor groups were also stained with CD31. Six-week old Ptenpc−/− mice were injected (i.p.) with either mcr84 (10 mg/kg) or EHT1864 (10 mg/kg) twice weekly for three weeks. The prostate glands were harvested and angiogenesis was analyzed using CD31 staining. No significant difference in staining among the groups indicating that the observed impact of these treatments is not caused by an effect of these compounds on angiogenesis.

Figures 5A, 5B, 5C, 5D, 5E:
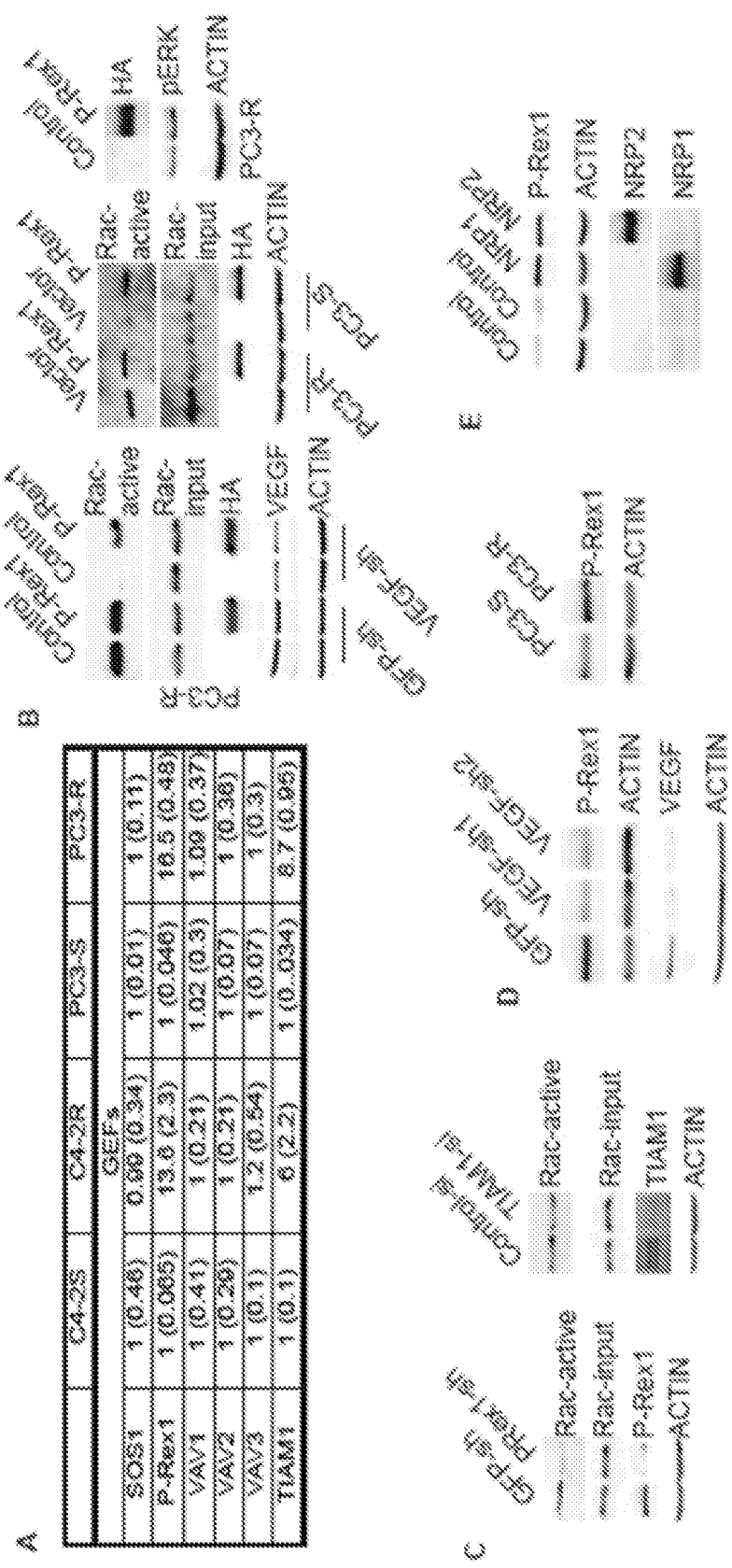
FIGS. 5A-5J. P-Rex1, a GEF, promotes Rac1 activation and resistance to VEGF/VEGFR-targeted therapy.
Figures 5F, 5G, 5H, 5I, 5J:
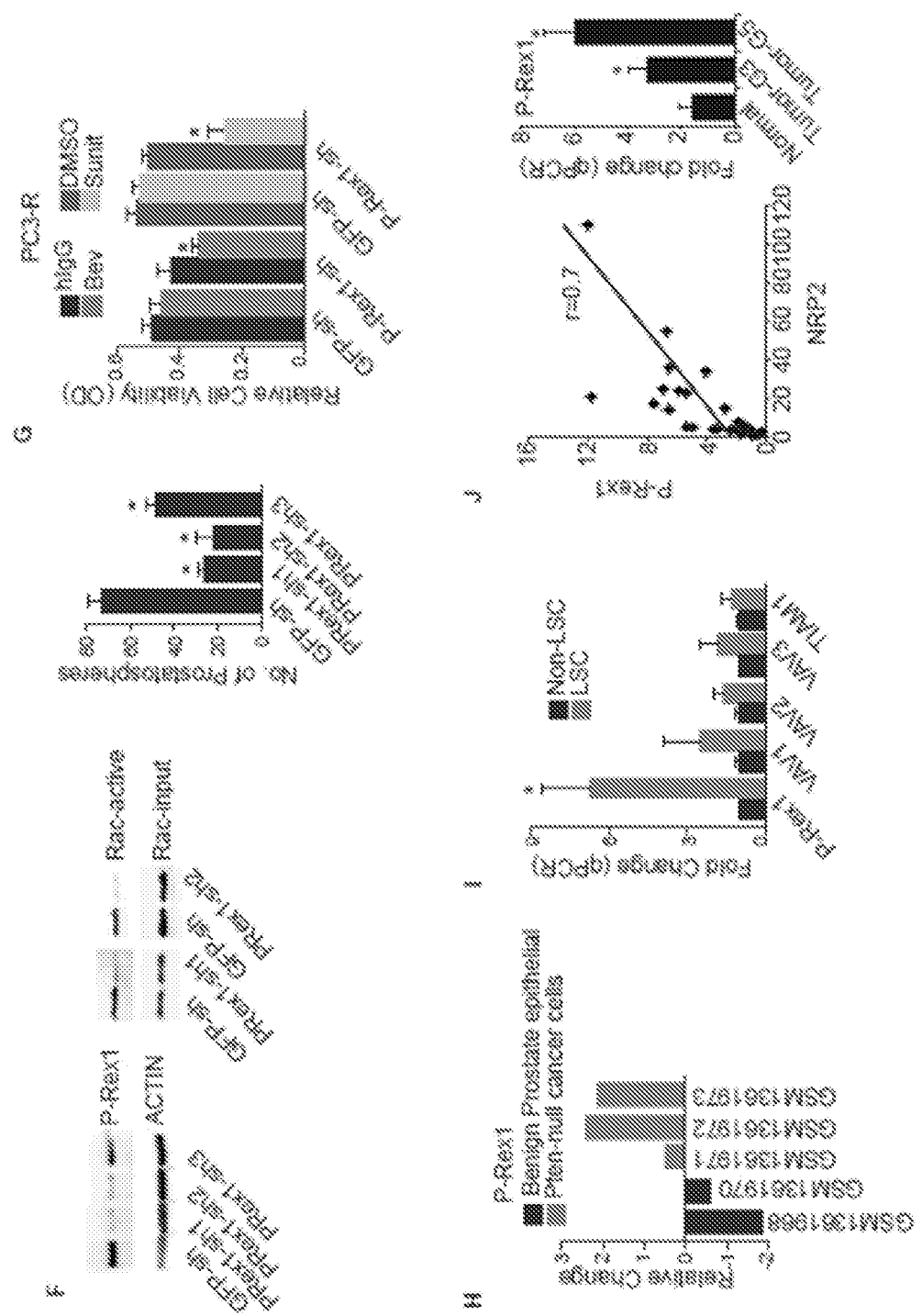
Figure 10:
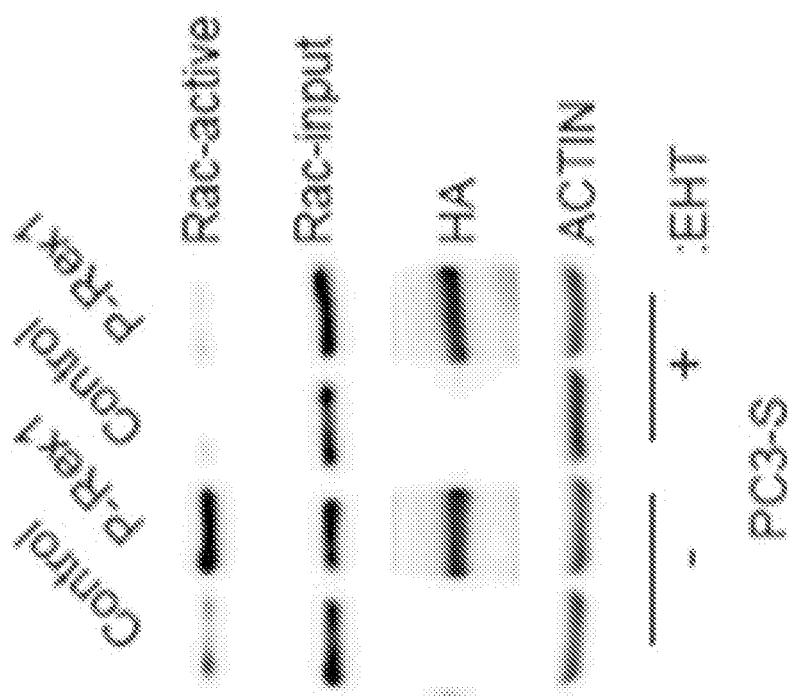
FIG. 10. P-Rex1 was expressed in sensitive PC3 cells. Cells were treated with EHT1864 and the effect on Rac activation was determined.

Identification of P-Rex1 as the Mediator of Resistance to VEGF/VEGFR-Targeted Therapy To understand how VEGF/NRP signaling activates Rac1 and promotes resistance to VEGF/VEGFR-targeted therapy, we compared the expression of potential guanine-nucleotide exchange factors (GEFs) known to be involved in Rac1 activity in sensitive and resistant cells (FIG. 5A). This screening revealed elevated expression of P-Rex1 and, to a lesser extent, TIAM1 in resistant cells (FIG. 5A). The importance of P-Rex1 in Rac1 activation is indicated by our finding that expression of exogenous P-Rex1 in VEGF-depleted resistant cells or in sensitive cells restored Rac1 activation (FIG. 5B and FIG. 10). In contrast, down-regulation of TIAM1 expression in resistant cells had no effect on Rac1 activation (FIG. 5C), suggesting that endogenous P-Rex1 is sufficient to maintain Rac1 activation even in the absence of TIAM1. For this reason, we focused subsequent experiments on P-Rex1. P-Rex1 expression is dependent upon VEGF/NRP signaling because down-regulation of VEGF significantly reduced P-Rex1 expression in resistant cells (FIG. 5D) and expression of either NRP1 or NRP2 in sensitive cells increased P-Rex1 expression (FIG. 5E). Moreover, depletion of P-Rex1 expression in resistant cells diminished Rac1 activity and prostatosphere formation (FIG. 5F). The importance of P-Rex1 in promoting resistance is indicated by the finding that down-regulation of P-Rex1 in resistant cells increased their sensitivity to bevacizumab and sunitinib (FIG. 5G).

Our P-Rex1 experimental results were validated by analyzing the gene expression profiles of epithelial cells microdissected from benign prostates and tumor cells from Pten-null prostate carcinomas. P-Rex1 expression is significantly elevated in cancer cells compared to benign epithelium (p=0.04) (FIG. 5H). We also compared the expression levels of Rac GEFs in LSC and non-LSC cells isolated from PTEN$^{pc-/-}$ prostate tumors. Among all of the GEFs analyzed, only P-Rex1 expression is increased significantly in LSC compared to non-LSC cells (FIG. 5I). P-Rex1 expression is higher in prostate adenocarcinoma compared to non-cancerous tissues. More specifically, we observed that P-Rex1 expression correlates with tumor grade (FIG. 5J), similar to NRP2 expression (8). In fact, a positive correlation between P-Rex1 and NRP2 expression was detected in a cohort of prostate tumors (FIG. 5J).

Figure 6A:
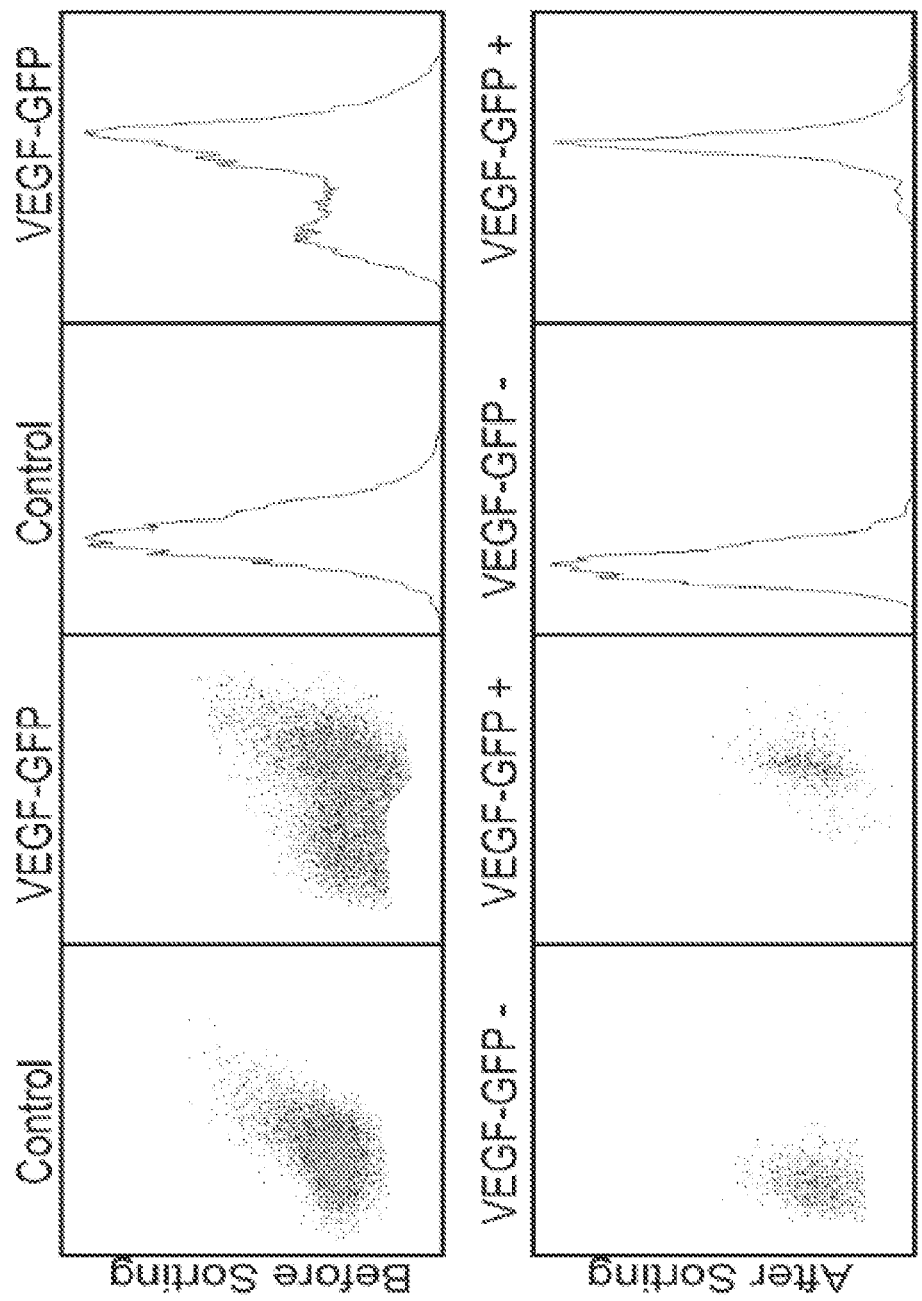
FIGS. 6A-6K. Rac1 is required for VEGF-mediated tumor initiation.
Figure 6C:
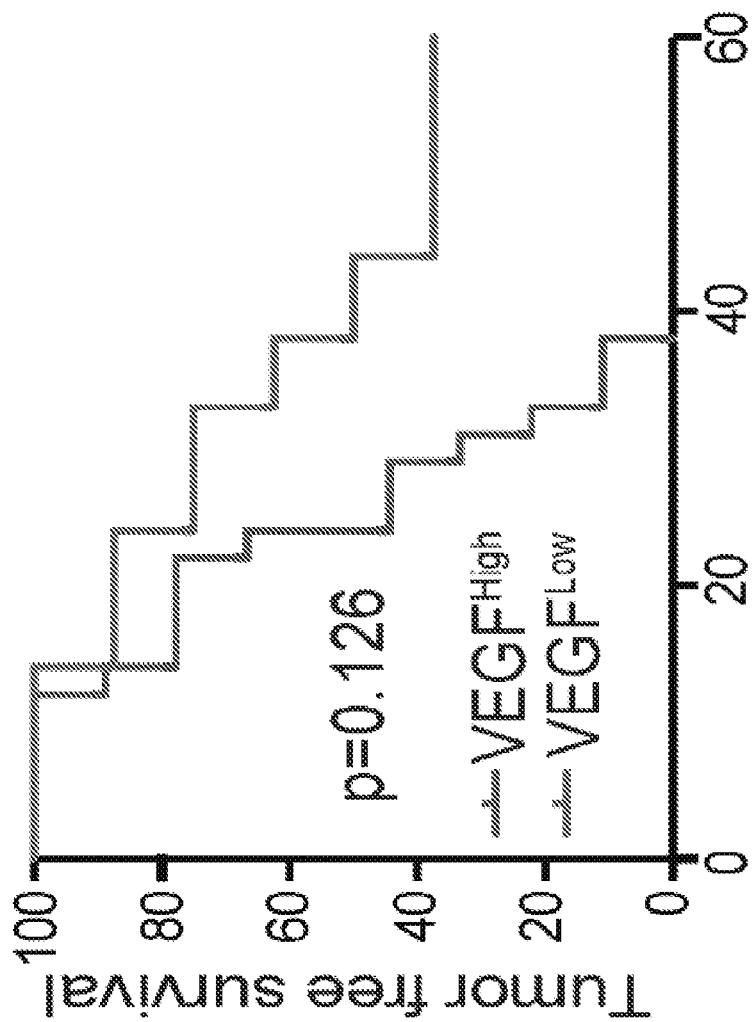
Figure 6B:
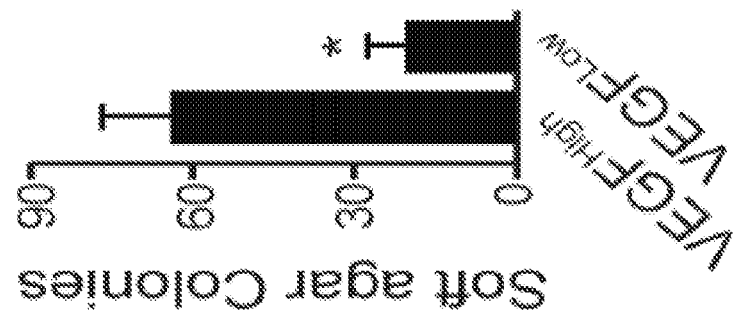
Figure 6D:
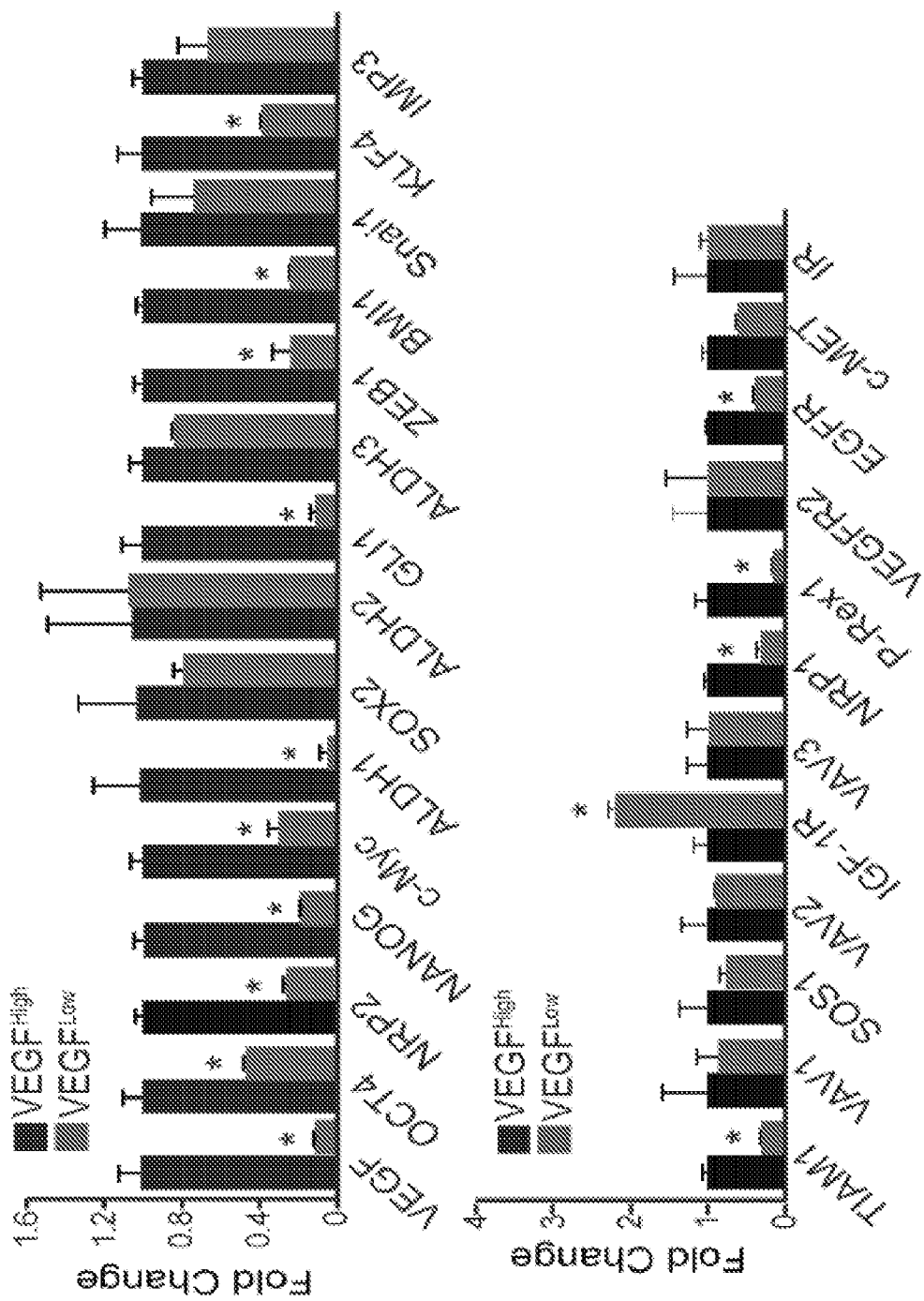
Figure 6E:
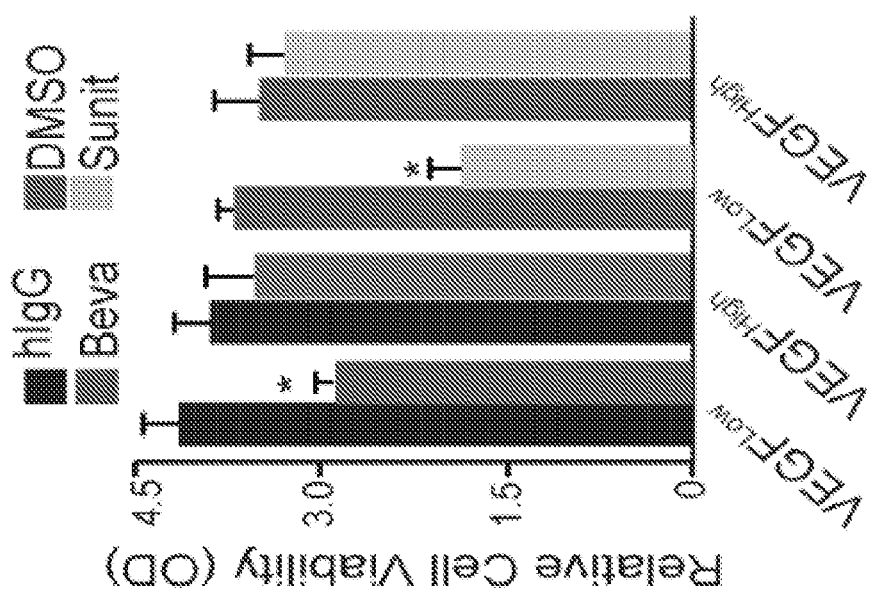
Figures 6F, 6G, 6H, 6I, 6J, 6K:
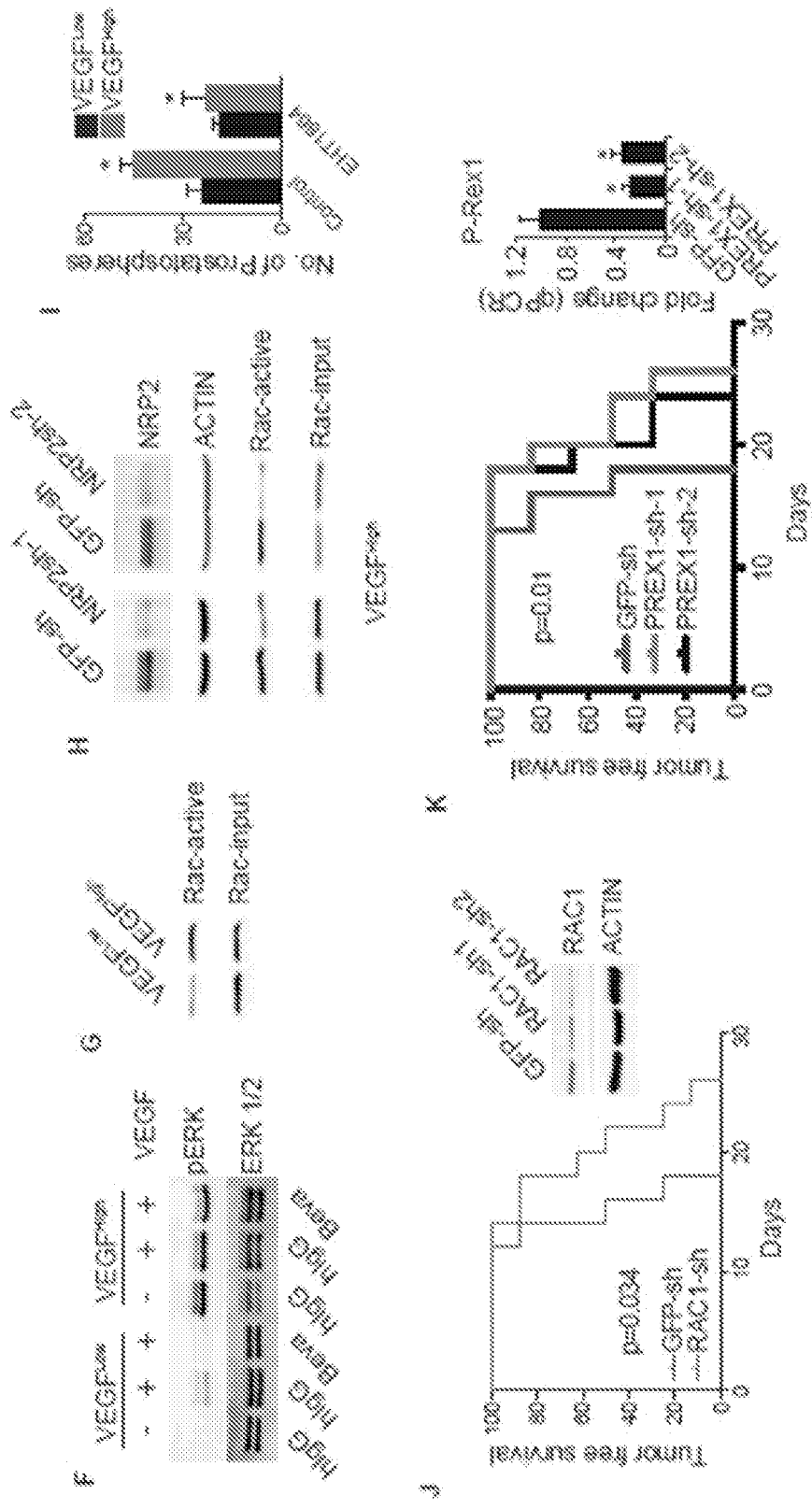

To demonstrate that VEGF-induced tumor initiation is dependent upon Rac1 activation, we engineered PC3 cells to express GFP under control of the VEGF promoter. We sorted these cells and generated two distinct populations designated VEGF$^{high}$ and VEGF$^{low}$ (FIG. 6A). VEGF$^{high}$ cells form more colonies in soft agar and initiate tumors more rapidly than VEGF$^{low}$ cells (FIGS. 6B-6C). Similar to the resistant cell lines described above, VEGF$^{high}$ cells express high levels of genes associated with CSCs, NRPs and P-Rex1 (FIG. 6D). Also the VEGF$^{high}$ cells are more resistant to bevacizumab and sunitinib compared to the VEGF$^{low}$ cells (FIG. 6E). VEGF induces ERK activation, which is inhibited by bevacuzimab in VEGF$^{low}$ cells (FIG. 6F). In contrast, VEGF$^{high}$ cells exhibit high basal ERK activation and this activation is resistant to bevacuzimab (FIG. 6F). VEGF$^{high}$ cells also exhibited increased Rac1 activity compared to the VEGF$^{low}$ cells (FIG. 6G). Also, down-regulation of NRP2 in VEGF$^{high}$ cells reduced Rac1 activation (FIG. 6H). Importantly, inhibition of Rac1 in VEGF$^{high}$ cells reduced their ability to form prostatospheres in vitro and tumors in vivo (FIGS. 6I-6J). Also, P-Rex1 down-regulation reduced tumor onset in vivo (FIG. 6K), confirming the crucial role of P-Rex1 in VEGF/NRP/Rac1 signaling. Taken together, these data substantiate the ability of VEGF/NRP2/P-Rex1 signaling to activate Rac1 and the importance of this pathway in tumor formation.

Figures 7A, 7B, 7C, 7D, 7E:
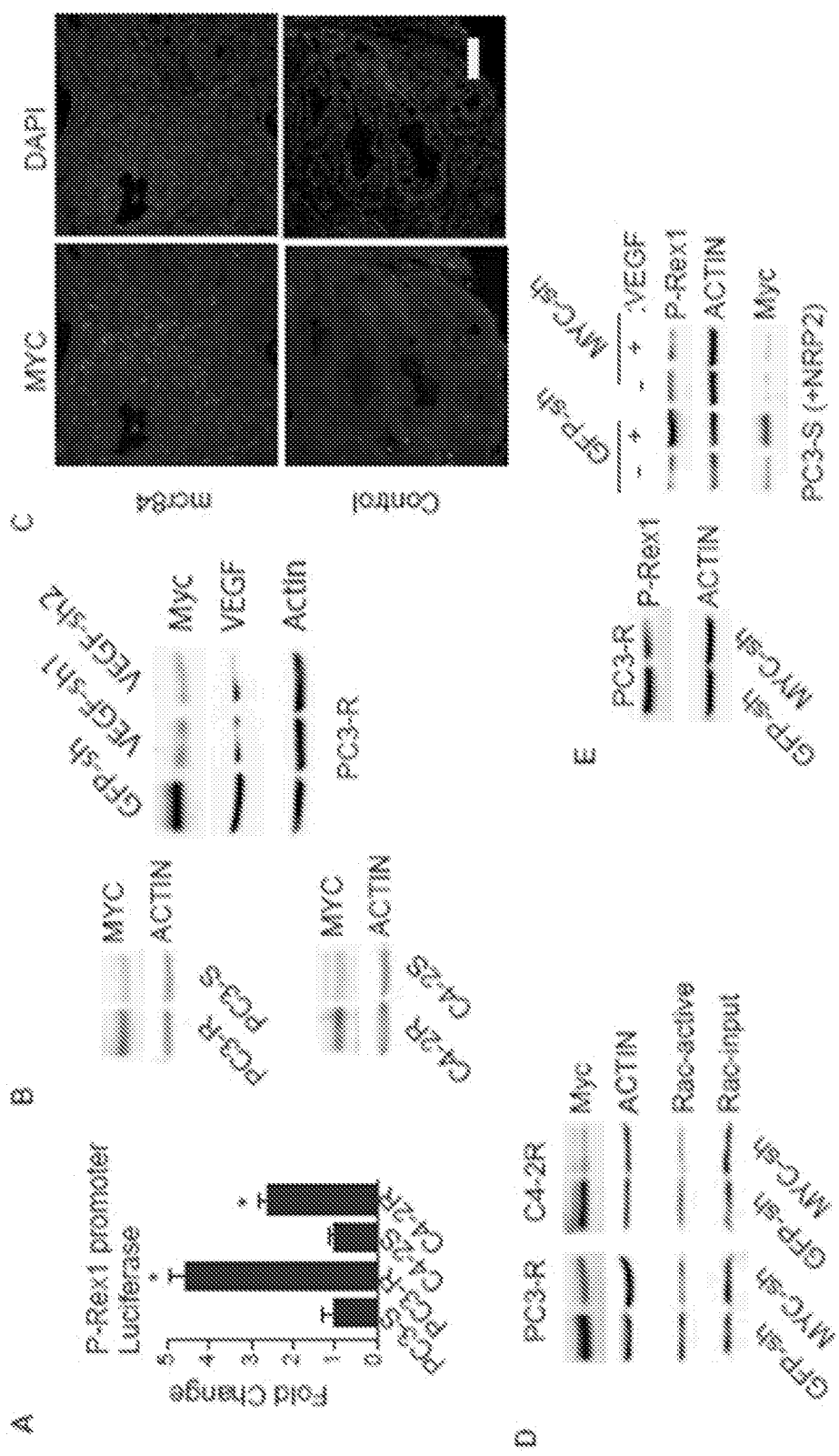
Figure 7F:
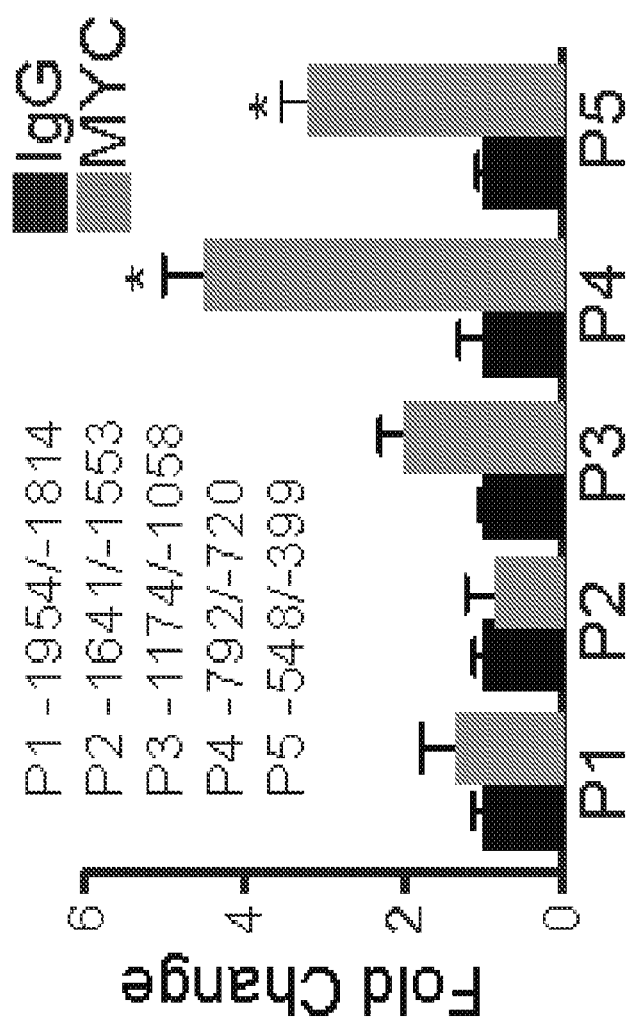
Figure 7G:
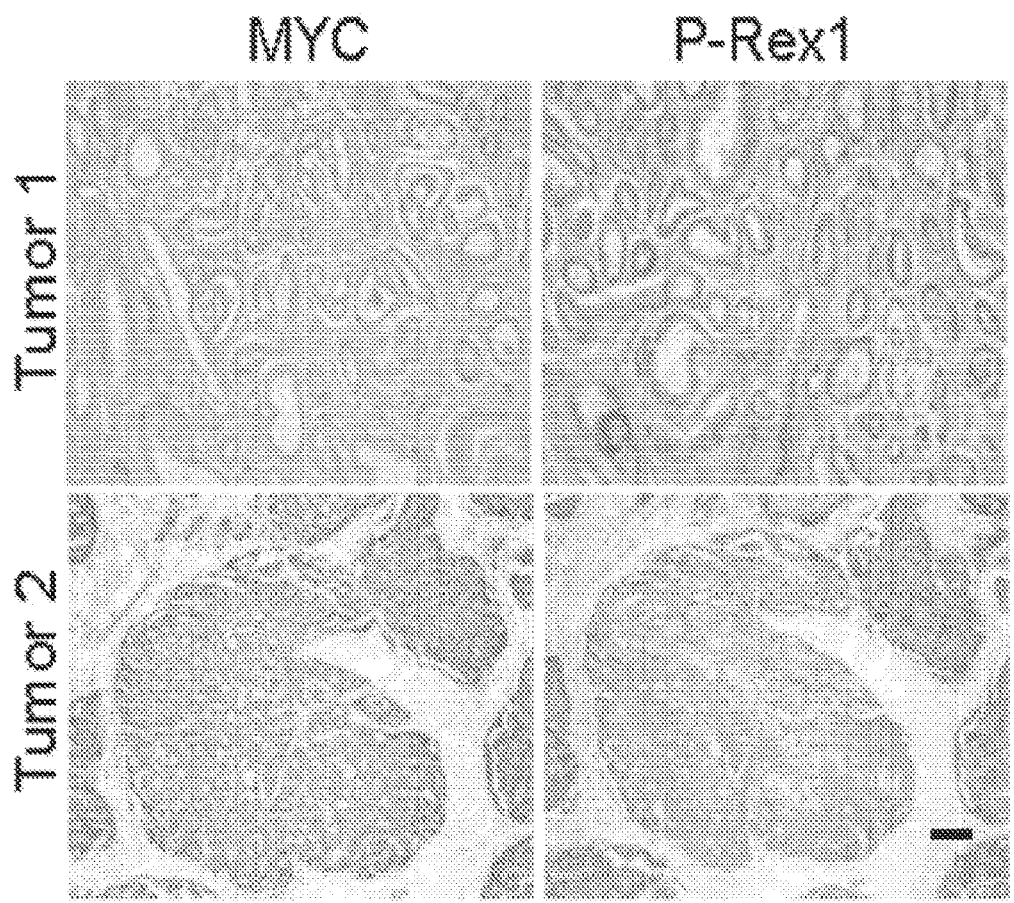
Figures 11A, 11B, 11C, 11D:
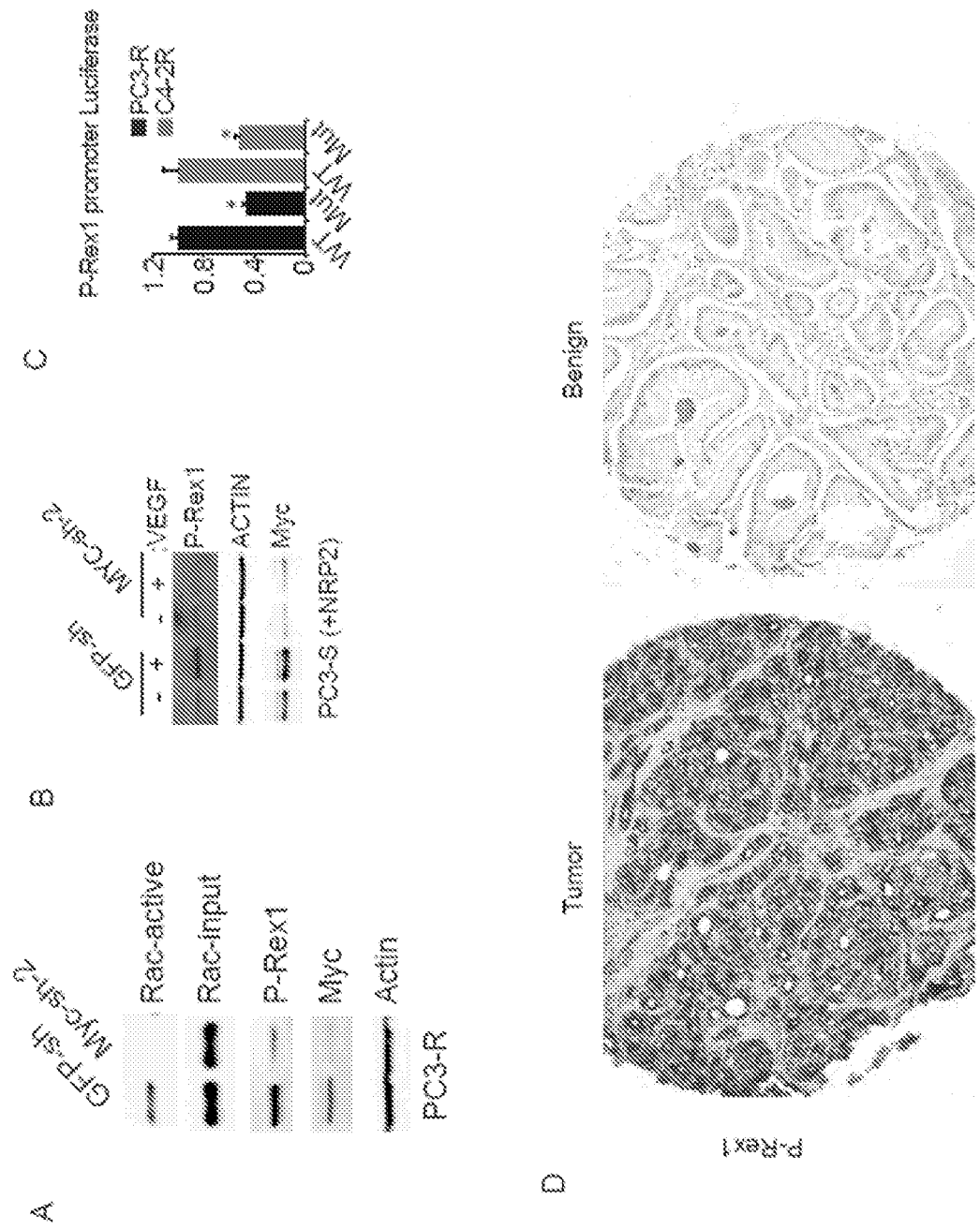
FIG. 11A. Myc expression was down-regulated in resistant PC3 cells using shRNA and the effect on Rac1 activation and P-Rex1 expression was determined.
FIG. 11B. NRP2 expressing PC3-S cells were transfected with either GFP-shRNA or Myc-shRNA, stimulated with VEGF (50 ng/ml) for 24 hours and the effect on P-Rex1 and Myc expression was measured.
FIG. 11C. PC3-R and C4-2R cells were transfected with a P-Rex1 promoter luciferase construct (WT or mutant) and *Renilla* luciferase (for normalization). Luciferase activity was measured and normalized to *Renilla*. Mutation was performed using the NEB site-directed mutagenesis kit.
FIG. 11D. The expression of P-Rex1 was analyzed in human prostate cancer specimens by IHC. Benign glands were negative for P-Rex1 staining validating the specificity of antibody and the induction of P-Rex1 expression in prostate cancer.

To identify the mechanism of P-Rex1 regulation, we focused on its transcriptional regulation because we observed increased activity of a luciferase reporter construct containing the P-Rex1 promoter in resistant cells compared to sensitive cells (FIG. 7A). We used the UCSC genome browser to search for putative transcription factor binding sites on the P-Rex1 promoter and identified Myc as a possible candidate. A role for Myc is supported by the increased expression of Myc in resistant compared to sensitive cell lines, as well as enrichment of Myc-positive cells in PTEN$^{pc-/-}$ tumors upon treatment with mcr84 (FIGS. 7B-7C). Moreover, Myc down-regulation reduced Rac1 activation and P-Rex1 expression in resistant cells (FIGS. 7D-7E and FIGS. 11A-11B). More definitively, we detected direct binding of Myc on the P-Rex1 promoter by ChIP (FIG. 7F), and mutation of a putative myc-binding site (CACTTG, −246) significantly reduced the activity of a luciferase promoter construct (FIG. 11C). We also found a significant correlation in P-Rex1 and Myc expression in human prostate cancer specimens by immunohistochemistry (FIG. 7G and FIG. 11D). These results infer that VEGF/NRP regulation of P-Rex1 is Myc-dependent. Indeed, we observed that VEGF was unable to induce P-Rex1 expression in the presence of Myc shRNA in PC3-S cells engineered to express NRP2 (FIG. 7E). Expression of Myc is VEGF-dependent based on the findings that down-regulation of VEGF reduced Myc expression and addition of VEGF increased Myc expression (FIGS. 7B, 7E).

Figure 7I:
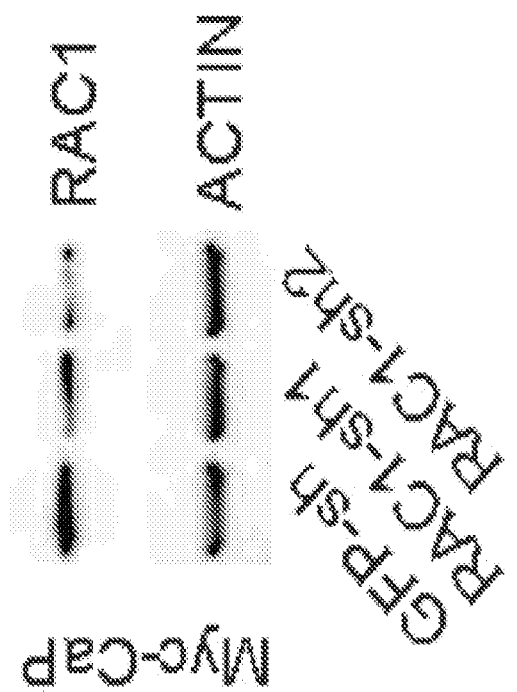
Figure 7H:
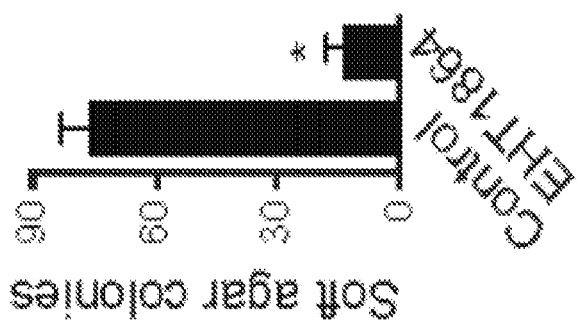

Myc is a regulator of prostate cancer and prostate-specific expression of a Myc transgene drives carcinogenesis in a step-wise fashion from PIN to invasive cancer. Myc-Cap cells were derived from this transgenic mouse model. Inhibition of Rac1 in Myc-CaP cells reduced their ability to form colonies in soft agar (FIG. 7H). Moreover, down-regulation of Rac1 or P-Rex-1 expression significantly increased tumor-free survival in vivo establishing the important role of Rac1/P-Rex1 in Myc-induced tumorigenesis (FIGS. 7I-7K).

For the immunoblots as shown in the figures described above, Table 1 shows normalized densitometric values of these immunoblots.

TABLE 1

| FIG. | | Lane 1 | Lane 2 | Lane 3 | Lane 4 | Lane 5 | lane 6 |
|---|---|---|---|---|---|---|---|
| | Normalized densitometric values of immunoblots | | | | | | |
| 2D | pERK | 0.24 | 1 | 0.22 | 0.31 | | |
| 2E | pERK | 0.19 | 0.53 | 1 | 0.95 | | |
| 2F | pERK | 0.22 | 0.19 | 1 | 0.86 | | |
| | pAKT | 1 | 0.94 | 1.04 | 1.02 | | |
| 2G | pERK | 0.12 | 0.1 | 1 | 1.05 | | |
| | pAKT | 1 | 1.07 | 1 | 0.92 | | |
| 2H | pERK | 0.34 | 1 | 1.04 | 1.02 | | |
| | pAKT | 1 | 0.98 | 1.1 | 0.98 | | |
| 2I | pERK | 0.14 | 1 | 0.96 | 0.94 | | |
| | pAKT | 1 | 0.99 | 1 | 1.02 | | |
| 2J | Active-Ras | 1 | 1.01 | 1 | 1.02 | | |
| 2K | Active-Ras | 0.35 | 1 | | | | |
| 2L, Left | pERK | 1 | 1.06 | | | | |
| 2L, Right | pERK | 1 | 0.97 | | | | |
| 3A | Rac-Active | 0.03 | 1 | 0.04 | 1 | | |
| 3B | pERK | 1 | 0.26 | 1.06 | 0.49 | | |
| 3C | Rac-Active | 1 | 0.99 | 0.26 | 0.31 | | |
| 3D | Rac-Active | 1 | 0.98 | 0.22 | 0.32 | | |
| 3E, Left | VEGF | 1 | 0.36 | 0.38 | | | |
| | Rac-Active | 1 | 0.41 | 0.44 | | | |
| 3E, Right | VEGF | 1 | 0.27 | 0.25 | | | |
| | Rac-Active | 1 | 0.18 | 0.21 | | | |
| 3F | Rac-Active | 0.13 | 1 | 0.54 | 1.09 | | |
| 5B, Left | Rac-Active | 1 | 1 | 0.15 | 0.54 | | |
| | VEGF | 1 | 1.03 | 0.36 | 0.4 | | |
| 5B, Middle | Rac-Active | 1 | 1.21 | 0.25 | 1.16 | | |
| 5B, Right | pERK | 0.58 | 1 | | | | |
| 5C, Left | Rac-Active | 1 | 0.37 | | | | |
| | P-Rex1 | 1 | 0.28 | | | | |
| 5C, Right | Rac-Active | 1 | 0.93 | | | | |
| | TIAM1 | 1 | 0.42 | | | | |
| 5D, Left | P-Rex1 | 1 | 0.37 | 0.4 | | | |
| | VEGF | 1 | 0.32 | 0.33 | | | |
| 5D, Right | P-Rex1 | 0.51 | 1 | | | | |
| 5E | P-Rex1 | 0.34 | 0.41 | 1 | 0.98 | | |
| 5F, Left | P-Rex1 | 1 | 0.21 | 0.23 | 0.81 | | |
| 5F, Right | Rac-Active | 1 | 0.42 | 1 | 0.37 | | |
| 6F | pERK | 0.11 | 0.29 | 0.15 | 1 | 0.91 | 0.89 |
| 6G | Rac-Active | 0.48 | 1 | | | | |
| 6H | NRP2 | 1 | 0.37 | 1 | 0.32 | | |
| | Rac-Active | 1 | 0.43 | 1 | 0.37 | | |
| 6J | RAC1 | 1 | 0.39 | 0.31 | | | |
| 7B, Left Upper | Myc | 1 | 0.41 | | | | |
| 7B, Left Lower | Myc | 1 | 0.39 | | | | |
| 7B, Right | Myc | 1 | 0.43 | 0.41 | | | |
| | VEGF | 1 | 0.44 | 0.45 | | | |
| 7D | Myc | 1 | 0.45 | 1 | 0.37 | | |
| | Rac-Active | 1 | 0.6 | 1 | 0.58 | | |
| 7E, Left | P-Rex1 | 1 | 0.51 | | | | |
| 7E, Right | P-Rex1 | 0.5 | 1 | 0.52 | 0.53 | | |
| | Myc | 0.49 | 1 | 0.38 | 0.39 | | |
| 7I | RAC1 | 1 | 0.48 | 0.41 | | | |

Example 2: Inhibiting P-Rex1 or RAC1 Improves the Effects of VEGF/VEGFR-Targeted Therapy in Colon Cancer Human colon tumor cells are harvested and isolated. These cells are sorted based on stem cell marker, and further exhibit resistance to bevacizumab treatment or sunitinib treatment. These tumor cell lines are further exposed to increasing concentrations of bevacizumab or sunitinib until bevacizumab or sunitinib no longer affects their survival.

Administering P-Rex1 inhibitor (e.g., P-Rex1 siRNA) or RAC1 inhibitor (e.g., EHT1864) can restore these cells' sensitivity to bevacizumab or sunitinib.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating prostate cancer that is resistant to VEGF/VEGFR-targeted therapy in a subject, the method comprising:
   administering to the subject a therapeutically effective amount of a VEGF/VEGFR-targeted therapy; and
   administering to the subject a therapeutically effective amount of a Ras-related C3 botulinum toxin substrate 1 (Rac1) inhibitor.

2. The method of claim 1, wherein the VEGF/VEGFR-targeted therapy is an anti-VEGF antibody or anti-VEGF binding antibody fragment.

3. The method of claim 1, wherein the VEGF/VEGFR-targeted therapy is bevacizumab, ranibizumab, mcr84, sunitinib, or pazopanib.

4. The method of claim 1, wherein the Rac1 inhibitor downregulates expression of Rac1.

5. The method of claim 4, wherein the Rac1 inhibitor is an antisense molecule, a small interfering RNA, or a small hairpin RNA which is specific for a nucleic acid encoding Rac1.

6. The method of claim 5, wherein the antisense molecule is an oligonucleotide.

7. The method of claim 1, wherein the Rac1 inhibitor is EHT1864, NSC23766, W56, or F56.

8. The method of claim 1, wherein the Rac1 inhibitor is a derivative of EHT1864 or NSC23766.

* * * * *

```
                           SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Primer Set 1, P1: Amplicon Size = 140 ;
      -1954/-1814

<400> SEQUENCE: 1
gttaccctgc cagttggatt                                           20

<210> SEQ ID NO 2
<211> LENGTH: 20
<212> TYPE: DNA
<213> ORGANISM: Artificial Sequence
<220> FEATURE:
<223> OTHER INFORMATION: Primer Set 1, P1: Amplicon Size = 140 ;
      -1954/-1814

<400> SEQUENCE: 2
tacctttctg agcctccgtt                                           20

<210> SEQ ID NO 3
<211> LENGTH: 20
<212> TYPE: DNA
<213> ORGANISM: Artificial Sequence
<220> FEATURE:
<223> OTHER INFORMATION: Primer Set 2, P2 : Amplicon Size = 88 ,
      -1641/-1553

<400> SEQUENCE: 3
aaggcccaga tcaaatgcta                                           20

<210> SEQ ID NO 4
<211> LENGTH: 20
<212> TYPE: DNA
<213> ORGANISM: Artificial Sequence
<220> FEATURE:
<223> OTHER INFORMATION: Primer Set 2, P2 : Amplicon Size = 88 ,
      -1641/-1553

<400> SEQUENCE: 4
aggacacagg gagagaatgg                                           20

<210> SEQ ID NO 5
<211> LENGTH: 20
<212> TYPE: DNA
<213> ORGANISM: Artificial Sequence
<220> FEATURE:
<223> OTHER INFORMATION: Primer Set 3, P3: Amplicon Size = 116 ,
      -1174/-1058

<400> SEQUENCE: 5
accatgatcg ttcccgttat                                           20

<210> SEQ ID NO 6
<211> LENGTH: 20
<212> TYPE: DNA
<213> ORGANISM: Artificial Sequence
```

-continued

```
<220> FEATURE:
<223> OTHER INFORMATION: Primer Set 3, P3: Amplicon Size = 116 ,
      -1174/-1058

<400> SEQUENCE: 6
gtcagctgct caggttcaaa                                               20

<210> SEQ ID NO 7
<211> LENGTH: 20
<212> TYPE: DNA
<213> ORGANISM: Artificial Sequence
<220> FEATURE:
<223> OTHER INFORMATION: Primer Set 4, P4: Amplicon Size = 71 -792/--720

<400> SEQUENCE: 7
gaaaggaaac gggaaagaga                                               20

<210> SEQ ID NO 8
<211> LENGTH: 19
<212> TYPE: DNA
<213> ORGANISM: Artificial Sequence
<220> FEATURE:
<223> OTHER INFORMATION: Primer Set 4, P4: Amplicon Size = 71 -792/--720

<400> SEQUENCE: 8
ctaccacgac cttgggaag                                                19

<210> SEQ ID NO 9
<211> LENGTH: 18
<212> TYPE: DNA
<213> ORGANISM: Artificial Sequence
<220> FEATURE:
<223> OTHER INFORMATION: Primer Set 5, P5: Amplicon Size = 149 -548/-399

<400> SEQUENCE: 9
tttacttggc ccgagcag                                                 18

<210> SEQ ID NO 10
<211> LENGTH: 19
<212> TYPE: DNA
<213> ORGANISM: Artificial Sequence
<220> FEATURE:
<223> OTHER INFORMATION: Primer Set 5, P5: Amplicon Size = 149 -548/-399

<400> SEQUENCE: 10
gaaccgagcg taccaactc                                                19
```